US006969399B2

(12) United States Patent
Schock et al.

(10) Patent No.: US 6,969,399 B2
(45) Date of Patent: Nov. 29, 2005

(54) APPARATUS FOR ALTERING THE BODY TEMPERATURE OF A PATIENT

(75) Inventors: Robert B. Schock, Sparta, NJ (US); Robert J. Freedman, Jr., Alexandria, LA (US); Marc Cote, Cornwall, NY (US)

(73) Assignee: Life Recovery Systems HD, LLC, Alexandria, LA (US)

( * ) Notice: Subject to any disclaimer, the term of this patent is extended or adjusted under 35 U.S.C. 154(b) by 82 days.

(21) Appl. No.: 10/193,635

(22) Filed: Jul. 11, 2002

(65) Prior Publication Data

US 2004/0225341 A1 Nov. 11, 2004

(51) Int. Cl.⁷ .................................................. A61F 7/00
(52) U.S. Cl. ...................................... 607/108; 607/112
(58) Field of Search ................... 607/96, 104, 108–112, 607/107

(56) References Cited

U.S. PATENT DOCUMENTS

| | | | |
|---|---|---|---|
| 998,804 A | 7/1911 | Salisbury | |
| 1,936,960 A | 11/1933 | Bowman | |
| 2,043,721 A | 6/1936 | Warwick | |
| 2,093,834 A | 9/1937 | Gaugler | |
| 2,224,876 A | 12/1940 | Matys | |
| 2,272,481 A | * 2/1942 | Rinkes | 601/166 |
| 2,416,788 A | 3/1947 | Andrews | |
| 2,493,067 A | 1/1950 | Goldsmith | |
| 2,556,600 A | 9/1951 | Colon | |
| 2,702,552 A | 2/1955 | Moodie | |
| 2,832,336 A | 4/1958 | Davis et al. | |
| 3,051,180 A | 8/1962 | Adams-Ray et al. | |
| 3,266,064 A | 8/1966 | Figman | |
| 3,477,424 A | 11/1969 | Tracy | |
| 3,587,577 A | 6/1971 | Smimov et al. | |
| 3,757,362 A | 9/1973 | Bowlin et al. | |

(Continued)

FOREIGN PATENT DOCUMENTS

| | | |
|---|---|---|
| GB | 1095988 | 12/1967 |
| JP | 10/033626 | 2/1998 |
| WO | WO 88/10074 A1 | 12/1988 |
| WO | WO 94/05238 A1 | 3/1994 |
| WO | WO 96/13234 A1 | 5/1996 |
| WO | WO 98/40039 A1 | 9/1998 |

(Continued)

OTHER PUBLICATIONS

Blair, D., et al., *The Increase in Tone in Forearm Resistance Blood Vessels Exposed to Increased Transmural Pressure*, The Journal of Physiology, Jul. 1959, pp. 614–625, vol. 149, Cambridge University Press, London, Great Britain.

(Continued)

*Primary Examiner*—Roy D. Gibson
(74) *Attorney, Agent, or Firm*—Senniger Powers

(57) ABSTRACT

An apparatus for adjusting the body temperature of a patient comprises an enclosure defining an interior space for receiving at least a portion of a patient's body therein. The enclosure is adapted for substantially sealingly enclosing the portion of the patient's body within the interior space with the enclosure. Heat transfer liquid may then be circulated through the interior space of the enclosure via an inlet and an outlet for flow over the patient's body in direct liquid contact therewith to promote heat transfer between the patient's body and said heat transfer liquid. The heat transfer liquid may be either warmer or cooler than the patient's body temperature, to either warm or cool the portion. Controlled cooling may be employed to induce therapeutic hypothermia, while controlled warming may be employed to counteract unintended hypothermia. The apparatus further comprises a portable control unit that includes a liquid delivery system, a power source, a control system and a user interface for powering and controlling the liquid delivery system.

75 Claims, 16 Drawing Sheets

U.S. PATENT DOCUMENTS

| | | | |
|---|---|---|---|
| 4,057,861 A | | 11/1977 | Howorth |
| 4,074,369 A | | 2/1978 | Harmon |
| 4,141,585 A | | 2/1979 | Blackman |
| 4,149,529 A | * | 4/1979 | Copeland et al. ............. 601/17 |
| 4,300,547 A | | 11/1981 | Pasternack |
| 4,353,359 A | * | 10/1982 | Milbauer .................... 601/166 |
| 4,376,437 A | * | 3/1983 | Sundheim et al. ............. 602/2 |
| 4,572,188 A | | 2/1986 | Augustine et al. |
| 4,586,500 A | | 5/1986 | Glynn |
| 4,648,392 A | | 3/1987 | Cartier et al. |
| 4,691,762 A | | 9/1987 | Elkins et al. |
| 4,738,119 A | | 4/1988 | Zafred |
| 4,747,408 A | * | 5/1988 | Chuan-Chih ................. 607/83 |
| 4,765,338 A | | 8/1988 | Turner et al. |
| 4,858,259 A | | 8/1989 | Simmons et al. |
| 4,865,012 A | | 9/1989 | Kelley |
| 4,884,304 A | | 12/1989 | Elkins |
| 4,945,901 A | * | 8/1990 | Burcke, Jr. ................. 601/157 |
| 4,959,877 A | | 10/1990 | Covil |
| 4,962,761 A | | 10/1990 | Golden |
| 4,987,618 A | | 1/1991 | Tolbert |
| 4,987,896 A | | 1/1991 | Nakamatsu |
| 5,016,304 A | | 5/1991 | Ryhiner |
| 5,033,136 A | | 7/1991 | Elkins |
| 5,063,924 A | | 11/1991 | Galvan et al. |
| 5,074,285 A | | 12/1991 | Wright |
| 5,146,625 A | | 9/1992 | Steele et al. |
| 5,149,331 A | | 9/1992 | Ferdman et al. |
| 5,172,689 A | | 12/1992 | Wright |
| 5,235,709 A | | 8/1993 | Terlep |
| 5,241,958 A | | 9/1993 | Noeldner |
| 5,243,706 A | | 9/1993 | Frim et al. |
| 5,249,318 A | | 10/1993 | Loadsman |
| 5,257,429 A | | 11/1993 | Genis |
| 5,261,399 A | | 11/1993 | Klatz et al. |
| 5,265,599 A | | 11/1993 | Stephenson et al. |
| 5,292,347 A | | 3/1994 | Pompei |
| 5,295,949 A | | 3/1994 | Hathaway |
| 5,300,100 A | | 4/1994 | Hickle et al. |
| 5,305,471 A | | 4/1994 | Steele et al. |
| D347,491 S | | 5/1994 | Holloway |
| 5,336,250 A | | 8/1994 | Augustine |
| 5,342,411 A | | 8/1994 | Maxted et al. |
| 5,350,417 A | | 9/1994 | Augustine |
| 5,358,467 A | | 10/1994 | Milstein et al. |
| 5,383,918 A | | 1/1995 | Panetta |
| 5,411,494 A | | 5/1995 | Rodriguez |
| 5,416,935 A | | 5/1995 | Nieh |
| 5,441,477 A | | 8/1995 | Hargest |
| 5,496,357 A | | 3/1996 | Jensen et al. |
| 5,507,792 A | | 4/1996 | Mason et al. |
| 5,584,084 A | | 12/1996 | Klearman et al. |
| 5,603,728 A | | 2/1997 | Pachys |
| 5,603,729 A | | 2/1997 | Brown et al. |
| 5,609,619 A | | 3/1997 | Pompei |
| 5,642,539 A | | 7/1997 | Kuo |
| 5,683,438 A | | 11/1997 | Grahn |
| 5,688,225 A | | 11/1997 | Walker |
| 5,722,482 A | | 3/1998 | Buckley |
| 5,755,756 A | | 5/1998 | Freedman, Jr. et al. |
| 5,800,480 A | | 9/1998 | Augustine et al. |
| 5,817,147 A | | 10/1998 | Wolf |
| 5,871,526 A | | 2/1999 | Gibbs et al. |
| 5,879,316 A | | 3/1999 | Safar et al. |
| 5,887,304 A | | 3/1999 | von der Heyde |
| 5,906,588 A | | 5/1999 | Safar et al. |
| 5,913,885 A | | 6/1999 | Klatz et al. |
| 5,913,886 A | | 6/1999 | Soloman |
| 5,927,273 A | | 7/1999 | Federowicz et al. |
| 5,950,234 A | | 9/1999 | Leong et al. |
| 5,957,964 A | | 9/1999 | Ceravolo |
| 5,975,081 A | | 11/1999 | Hood et al. |
| 5,980,561 A | * | 11/1999 | Kolen et al. ................. 607/104 |
| 5,991,948 A | | 11/1999 | Stanley et al. |
| 6,004,662 A | | 12/1999 | Buckley |
| 6,030,412 A | | 2/2000 | Klatz et al. |
| 6,052,853 A | | 4/2000 | Schmid |
| 6,109,338 A | | 8/2000 | Butzer |
| 6,117,164 A | | 9/2000 | Gildersleeve et al. |
| 6,149,674 A | | 11/2000 | Borders |
| 6,165,208 A | | 12/2000 | Reyes et al. |
| 6,182,316 B1 | * | 2/2001 | Thomas et al. ................. 5/22 |
| 6,183,855 B1 | | 2/2001 | Buckley |
| 6,188,930 B1 | | 2/2001 | Carson |
| 6,197,045 B1 | | 3/2001 | Carson |
| 6,210,427 B1 | | 4/2001 | Augustine et al. |
| 6,228,106 B1 | | 5/2001 | Simbruner et al. |
| 6,238,427 B1 | | 5/2001 | Matta |
| 6,245,094 B1 | | 6/2001 | Pompei |
| 6,276,155 B2 | | 8/2001 | Siman-Tov et al. |
| 6,277,144 B1 | | 8/2001 | Tomic-Edgar et al. |
| 6,352,550 B1 | | 3/2002 | Gildersleeve et al. |
| 6,375,674 B1 | | 4/2002 | Carson |
| 6,461,379 B1 | | 10/2002 | Carson et al. |
| 6,508,831 B1 | * | 1/2003 | Kushnir ...................... 607/104 |
| 6,517,510 B1 | * | 2/2003 | Stewart et al. ................. 604/31 |
| 6,520,982 B1 | | 2/2003 | Boynton et al. |
| D471,987 S | | 3/2003 | Hoglund et al. |
| D472,322 S | | 3/2003 | Hoglund et al. |
| 6,551,347 B1 | | 4/2003 | Elkins |
| D474,544 S | | 5/2003 | Hoglund et al. |
| 6,565,593 B2 | * | 5/2003 | Diana ......................... 607/108 |
| 6,602,277 B2 | | 8/2003 | Grahn et al. |
| 6,620,187 B2 | | 9/2003 | Carson et al. |
| 6,645,232 B2 | | 11/2003 | Carson |
| 6,648,905 B2 | | 11/2003 | Hoglund et al. |
| D483,125 S | | 12/2003 | Hoglund et al. |
| 6,660,027 B2 | | 12/2003 | Gruszecki et al. |
| 6,669,715 B2 | | 12/2003 | Hoglund et al. |
| 6,673,099 B2 | * | 1/2004 | Grahn et al. ................. 607/108 |
| 6,682,550 B2 | | 1/2004 | Clifton et al. |
| 6,685,731 B2 | * | 2/2004 | Kushnir et al. ............. 607/104 |
| 6,692,518 B2 | | 2/2004 | Carson |
| 6,695,872 B2 | | 2/2004 | Elkins |
| 6,699,267 B2 | | 3/2004 | Voorhees et al. |
| 6,718,785 B2 | | 4/2004 | Bieberich |
| 6,730,115 B1 | | 5/2004 | Heaton |
| 6,749,624 B2 | | 6/2004 | Knowlton |
| 6,764,502 B2 | | 7/2004 | Bieberich |
| 6,799,063 B2 | | 9/2004 | Carson |
| 6,800,087 B2 | | 10/2004 | Papay et al. |
| 6,818,012 B2 | | 11/2004 | Ellingboe |
| 2002/0007201 A1 | | 1/2002 | Grahn et al. |
| 2002/0193852 A1 | | 12/2002 | Renfro |
| 2003/0024684 A1 | | 2/2003 | Lyons et al. |
| 2003/0097163 A1 | * | 5/2003 | Kane et al. ................. 607/108 |
| 2003/0125649 A1 | * | 7/2003 | McIntosh et al. ............. 601/15 |
| 2003/0229385 A1 | | 12/2003 | Elkins |
| 2003/0236561 A1 | | 12/2003 | Lennox |
| 2004/0049252 A1 | | 3/2004 | Gluderer |
| 2004/0127964 A1 | | 7/2004 | Grahn et al. |
| 2004/0133253 A1 | | 7/2004 | Grahn et al. |
| 2004/0187512 A9 | | 9/2004 | Becker et al. |

FOREIGN PATENT DOCUMENTS

| | | |
|---|---|---|
| WO | WO 99/09916 A1 | 3/1999 |
| WO | WO 99/39678 A1 | 8/1999 |
| WO | WO 99/44552 A1 | 9/1999 |
| WO | WO 01/50988 A1 | 7/2001 |

OTHER PUBLICATIONS

Wolthuis R., et al., *Physiological Effects of Locally Applied Reduced Pressure in Man*, Physiological Reviews, 1974, pp. 566–595, vol. 54, The American Physiological Society, Bethesda, Maryland, United States.

Henriksen, O., *Sympathetic reflex control of blood flow in human peripheral tissues*, ACTA Physiologica Scandinavica, 1991, pp. 33–39, vol. 143 Supplement 603, ACTA Physiologica Scandinavica, Stockholm, Sweden.

Grahn, D. et al., *Recovery from mild hypothermia can be accelerated by mechanically distending blood vessels in the hand*, Journal of Applied Physiology, Nov. 1998, pp. 1643–1648, vol. 85 No. 5, American Physiological Society, Bethesda, Maryland, United States.

Howard, E., et al., *Can recovery from mild hypothermia be accelerated so much by mechanically distending locally heated blood vessels?*, Journal of Applied Physiology, Aug. 1999, pp. 867–868, vol. 87 No. 2, American Physiological Society, Bethesda, Maryland, United States.

Felberg, R., et al., *Hypothermia After Cardiac Arrest: Feasibility and Safety of an External Cooling Protocol*, Circulation, 2001, pp. 1799–1804, vol. 104, American Heart Association, Dallas, Texas, United States.

Taguchi, A., et al., *Negative Pressure Rewarming vs. Forced Air Warming in Hypothermic Postanesthetic Volunteers*, Anesthesia & Analgesia, Jan. 2001, pp. 261–266, vol. 92 No. 1, International Anesthesia Research Society et al., San Francisco, California, United States.

Bernard, S.A., et al., *Treatment of Comatose Survivors of Out-of-Hospital Cardiac Arrest with Induced Hypothermia*, New England Journal of Medicine, Feb. 21, 2002, pp. 557–563, vol. 346 No. 8, Massachusetts Medical Society, Boston, Massachusetts, United States.

Holzer, M., et al., *Mild Therapeutic Hypothermia to Improve the Neurologic Outcome after Cardiac Arrest*, New England Journal of Medicine, Feb. 21, 2002, pp. 549–556, vol. 346 No. 8, Massachusetts Medical Society, Boston, Massachusetts, United States.

Henricksen, O., *Local Sympathetic Reflex Mechanism in Regulation of Blood Flow in Human Subcutaneous AdiposeTissue*, ACTA Physiologica Scandinavica, 1977, 48 pages, Supplement 450, Almqvist & Wiksell, Uppsala, Sweden.

William E. Lawson, et al., "Benefits are Sustained at 3–year Follow–up in Patients Who Have Been Treated With Enhanced External Counterpulsation," Mar. 13, 1994, pp. 1.

Laura Gordon, "Blood–pump Cuffs Curb Angina," Apr. 21, 1994, pp. 1.

W.E. Lawson, et al., "Efficacy of Enhanced External Counter–pulsation in the Treatment of Angina Pectoris," 1992, pp. 1.

William E. Lawson, M.D. et al., "Efficacy of Enhanced External Counterpulsation in the Treatment of Angina Pectoris," Oct. 1, 1992, pp. 859–862.

Author Unknown, "Enhanced External Counterpulsation (EECP)," date unknown, pp. 130.

Future Medical Products, Inc., "Enhanced External Counterpulsation (EECP) Fact Sheet," Mar. 1994, pp. 1–3.

Zvi Oster, M.D., "Guidelines for the Submission of Abstracts," Apr. 30, 1993, pp. 1.

Zhen–Sheng Zheng, et al., "New Sequential External Counterpulsation for the Treatment of Acute Myocardial Infarction," Aug. 1984, pp. 470–476.

Zhen–Sheng Zbeng, et al., "Sequential External Counterpulsation (SECP) in China," 1983, pp. 1–5.

Nesher et al., entitled "A novel thermoregulatory system maintains perioperative normothermia in children undergoing elective surgery", Paediatric Anaesthesia, 2001, pp 555–560.

Raven et al., entitled "Hemodynamic Changes During Whole Body Surface Cooling and Lower Body Negative Pressure", Aviation, Space, and Environmental Medicine, Jul. 1981, pp 387–391.

Mellergard, entitled "Changes in Human Intracerebral Temperature in Response to Different Methods of Brain Cooling", Neurosurgery, Oct. 1992, pp 671–677, vol. 31, No. 4.

Koscheyev et al., entitled "Augmentation of blood circulation to the fingers by warming distant body areas", European Journal of Applied Physiology and Occupational Physiology (2000), pp. 103–111, 82:.

Janicki et al., entitled "Comparison of Two Different Temperature Maintenance Strategies During Open Abdominal Surgery", Anesthesiology, Oct. 2001, pp 868–874, vol. 95.

Nag et al., entitled "Efficacy of a water–cooled garment for auxillary body cooling in heat", Ergonomics, 1998, pp 179–187, vol. 41, No. 2.

Grahn et al., entitled "Recovery from mild hypothermia can be accelerated by mechanically distending blood vessels in the hand", The American Physiological Society, 1998, pp 1643–1648.

Guyton, A.C., entitled "Body Temperature, Temperature Regulation, and Fever", Textbook of Medical Physiology, 1986, pp 859, W.B. Saunders Company.

Kirklin et al., entitled "Hypothermia, Circulatory Arrest, and Cardiopulmonary Bypass", Chapter 2, 1993, pp 113–114, vol. 1, Second Edition, Churchill Livingston.

Plattner et al., entitled "Efficacy of Intraoperative Cooling Methods", Anesthesiology, Nov. 1997, pp 1089–1095, vol. 87(5), printed from www.anesthesiology.org.

Effects of Inducted Hypothermia on Samatosensory Evoked Potentials in Patients with Chronic Spinal Cord Injury, Paraplegia 31, 730–741, 1993.

Gardella et al., "Lowering Body Temperature with a Cooling Suit as Symptomatic Treatment for Themosensitive Multiple Scherosis Patients", Ital. J. Neurol. Sci., 1995.

Syndulko et al., "Preliminary Evaluation of Lowering Tympani Temperature for the Symptomatic Treatment of Multiple Sclerosis", J. Neuro. Rehab., vol. 9, No. 4, 1995.

Ku et al., "Hemodynamic and Thermal Responses to Head and Neck Cooling in Men and Women", Am J. Phys Med Rehabil, 75:443–450, 1996.

Spinoff, "New Help for MS Patients" 1993.

"Acute Effects of Cooling in Multiple Sclerosis: Pilot Study to Compare Two Cooling Garments", 1995.

Flensner et al., "The Cooling–Suit: Case Studies of its Influence on Fatique Among Eight Individuals with Multiple Sclerosis", Journal of Advanced Nursing 37(6), 541–550, Mar. 2002.

Ku et al., "Physiologic and Functional Responses of MS Patients to Body Cooling", Multiple Sclerosis, Sep./Oct. 2000, 427–434.

Murray et al., "Effect of body temperature on visual evoked potential delay and visual perception in multiple sclerosis", Journal of Neurology, Neurosurgery, and Psychiatry, 1977, 40, 1083–1091.

Greenleaf, et al., Fluid–electrolyte shifts and thermoregulation: Rest and work in heat with head cooling, Aug. 1980, vol. 51, No. 8, ASEMCG 5(8):747–850.

* cited by examiner

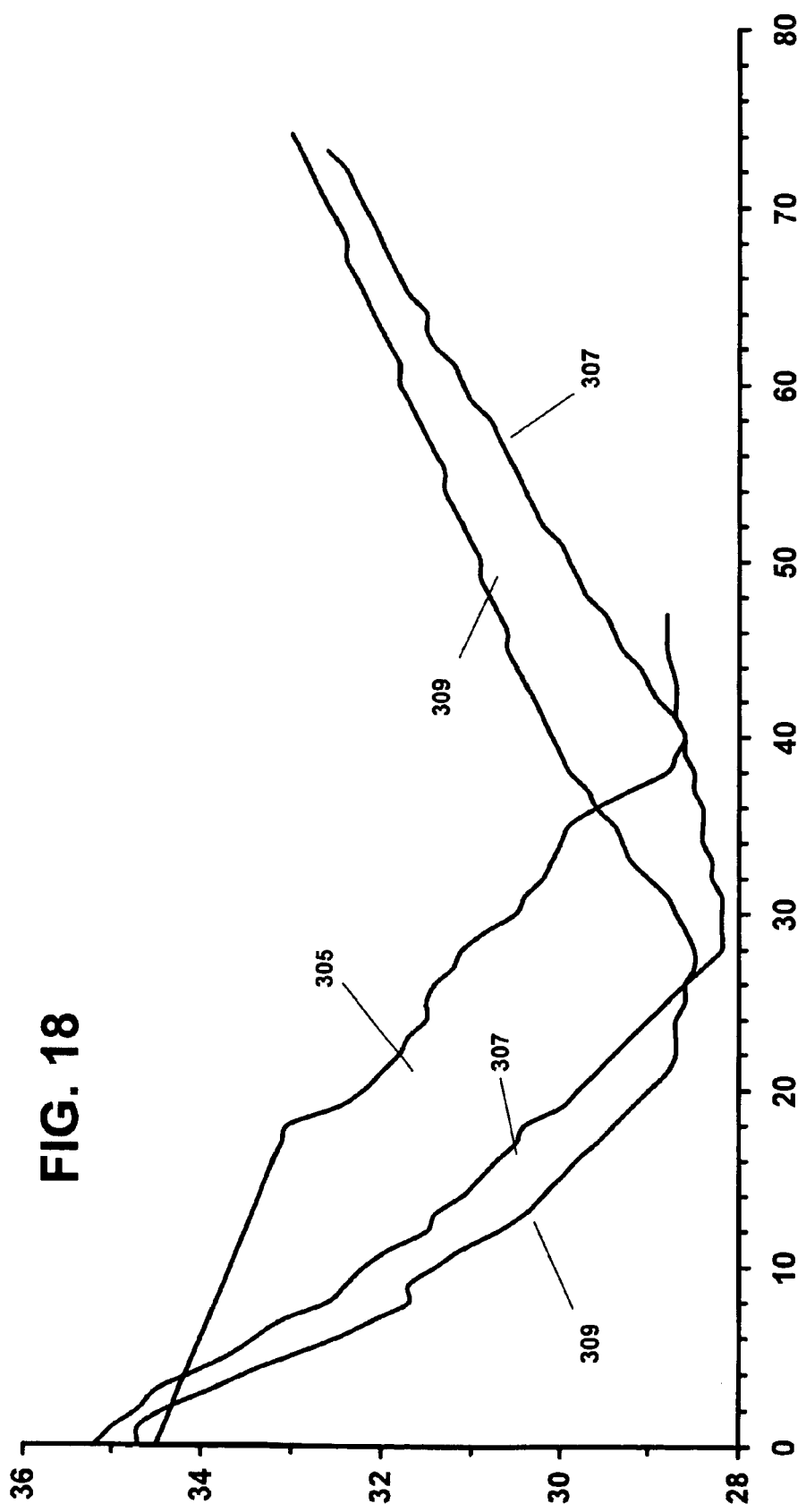

APPARATUS FOR ALTERING THE BODY TEMPERATURE OF A PATIENT

BACKGROUND OF THE INVENTION

This invention generally relates to medical apparatus for altering the body temperature of a patient and more particularly to apparatus that enables efficient, quick control of the body temperature of a patient, especially to induce hypothermia.

Sudden cardiac arrest remains a serious public health issue. Approximately 350,000 individuals are stricken in the United States annually, with overall survival rates of roughly 5 percent. Even with the immediate availability of the most advanced care currently available, including cardiopulmonary resuscitation (CPR), drugs, ventilation equipment, and automatic external defibrillators, a survival rate of 25 percent may be the probable best case scenario. Improved therapies to deal with this condition are clearly needed.

Numerous incidences of recovery following accidental hypothermia and cardiac arrest have been reported. This observation has led researchers to consider therapeutic hypothermia as a possible treatment for reducing the adverse consequences of circulatory arrest. Various studies have shown that moderate systemic hypothermia (approximately 3–5° C. (5.4–9.0° F.)) can reduce damage to vital organs, including the brain. Hypothermia induced both during and following cardiac arrest has demonstrated this benefit. The use of cardiopulmonary bypass has also been effective in rapidly achieving this goal. Direct flushing of cooled fluids into the arterial system has also been employed with success. Both invasive measures, however, require large bore intravascular catheters and rapid introduction of sterile solutions into the patient. Such invasive approaches have obvious disadvantages in dealing with out-of-hospital emergencies.

Noninvasive cooling, if sufficiently effective and portable, would be a preferable approach. Direct cooling of the head alone has produced variable results. However, post-resuscitative cooling of the entire body to approximately 33° C. (91.4° F.) by noninvasive treatment has been demonstrated to be surprisingly effective in recent clinical studies. The use of cold gel and ice packs produced cooling of approximately 0.9° C. (1.6° F.) per hour, and resulted in a nearly 100 percent improvement in neurologically intact survival (Bernard S.A. et al., *Treatment of Comatose Survivors of Out-of-Hospital Cardiac Arrest with Induced Hypothermia*, 346 NEW ENG. J. MED. 557–563 (2002)). In another study, cold air was found to be capable of cooling patients at a rate of about 0.25° C. (0.45° F.) per hour, which caused a 40 percent improvement in the same endpoint (Sterz F. et al., *Mild Therapeutic Hypothermia to Improve the Neurologic Outcome after Cardiac Arrest*, 346 NEW ENG. J. MED. 549–556 (2002)). In yet another study, a combination of water-filled cooling blankets and ice packs applied to the skin resulted in a cooling rate of 0.8° C. (1.4° F.) per hour (Felberg et al., *Hypothermia After Cardiac Arrest—Feasibility and Safety of an External Cooling Protocol*, 104 CIRCULATION 1799–1804 (2001)). Despite the success of these studies, increasing the rate of cooling may produce a higher rate of patient salvage.

Based on the current cooling procedures and systems, the present invention explores a unique solution to the problem of accelerated body cooling. Namely, the present invention is based upon the hypothesis that full body contact with a liquid medium, such as cold water, would induce high rates of heat transfer. Beyond immersion, controlling the liquid temperature and flow rate may allow further control of the cooling process, thereby producing a valuable system.

SUMMARY OF THE INVENTION

Among the several objects and features of the present invention may be noted the provision of an apparatus and method capable of decreasing the time required to induce hypothermia in a patient; the provision of an apparatus and method capable of controlled warming of a patient; the provision of such an apparatus and method that permits the delivery of CPR during cooling or warming; the provision of such an apparatus and method in which cooling liquid is brought into direct contact with skin; the provision of such an apparatus and method that allows for cooling or warming of the patient in a remote environment without electricity; and the provision of such an apparatus that allows for cooling or warming while the patient is in transport.

Generally, apparatus for adjusting the body temperature of a patient comprises an enclosure defining an interior space for receiving at least a portion of a patient's body therein. The enclosure is adapted for substantially sealingly enclosing the portion of the patient's body within the interior space. The enclosure has an inlet for receiving heat transfer liquid into the interior space for flow over the patient's body in direct liquid contact therewith to promote heat transfer between the patient's body and the heat transfer liquid. An outlet is in fluid communication with the interior space of the enclosure for exhausting the heat transfer liquid from the enclosure.

In another aspect of the present invention, an apparatus for adjusting the body temperature of a patient comprises an enclosure as set forth above adapted for enclosing the portion of the patient's body within the interior space with the enclosure generally contiguous with at least opposite sides of the portion of the patient's body. The enclosure further has an inlet and an outlet generally as set forth above.

In yet another aspect of the present invention, a method for controlling the body temperature of a patient comprises the step of substantially sealingly enclosing at least a portion of the patient's body within the interior space of an enclosure with the enclosure being generally contiguous with the portion of the patient's body. The method also requires directing a heat transfer liquid to flow within the interior space in direct liquid contact with the patient's body to promote heat transfer between the heat transfer liquid and the patient's body.

In still another aspect of the present invention, a method for controlling the body temperature of a patient comprises the steps of enclosing at least a portion of the patient's body within the interior space of an enclosure with at least opposite sides of the portion of the patient's body and directing a heat transfer liquid to flow generally as set forth above.

Other objects and features will be in part apparent and in part pointed out hereinafter.

BRIEF DESCRIPTION OF THE DRAWINGS

FIG. 18 is a graph of the internal body temperature of a swine subjected to different methods of cooling.

Corresponding reference characters indicate corresponding parts throughout the several views of the drawings.

DETAILED DESCRIPTION OF THE PREFERRED EMBODIMENT

Figure 1:
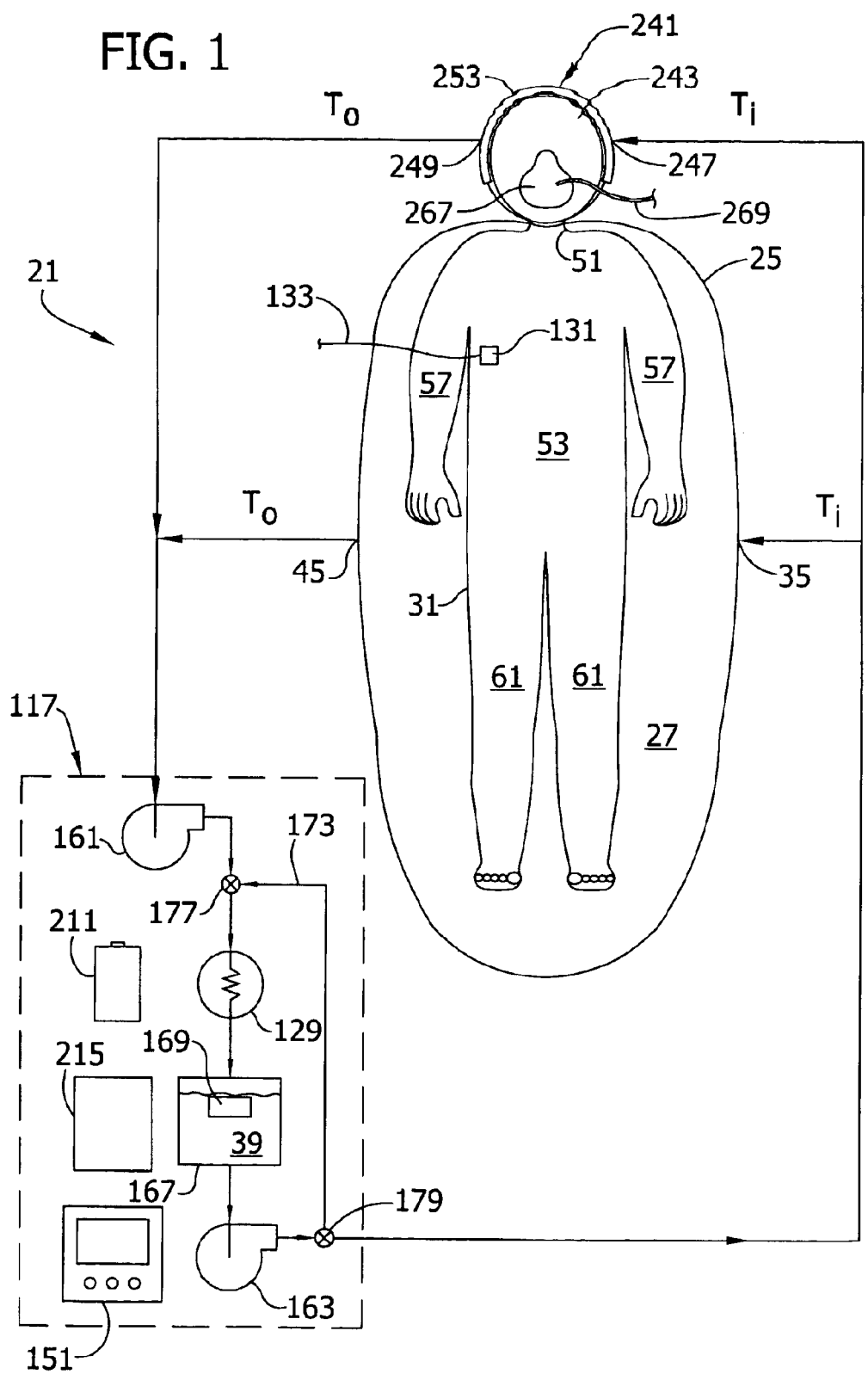
FIG. 1 is a schematic of apparatus of the present invention for altering the body temperature of a patient.

Referring now to the drawings and particularly to FIG. 1, reference number 21 generally indicates an apparatus for adjusting the body temperature of a patient. The apparatus 21 generally comprises an enclosure 25 defining an interior space 27 for receiving at least a portion 31 of a patient's body therein. The enclosure 25 is configured for substantially sealingly enclosing the portion 31 of the patient's body (illustrated in FIG. 1 as all of the patient's body below the head) within the interior space 27 with the enclosure generally contiguous with the patient's body. An inlet 35 of the enclosure 25 is adapted to receive heat transfer liquid 39, such as water, saline or other biocompatible liquids, into the enclosure. The inlet 35 is further in fluid communication with the interior space 27 of the enclosure 25 to direct heat transfer fluid 39 into the interior space 27 for flowing over the patient's body portion 31 in direct contact therewith to promote heat transfer between the patient's body portion and the heat transfer liquid. The enclosure 25 also has an outlet 45 in fluid communication with the interior space 27 of the enclosure for exhausting the heat transfer liquid 39 from the enclosure. More particularly, the enclosure 25 is adapted to generally conform to the portion of the patient's body 31 disposed within the interior space 27. Additionally, the inlet 35 and outlet 45 are positioned on the enclosure such that upon enclosure of the patient's body portion 31 within the interior space 27, the inlet faces a side of the patient's body portion opposite the outlet. Although any portion of the patient's body may be placed inside the enclosure 25, preferably the portion enclosed includes the body of the patient from the neck 51 of the patient downward, including the torso 53, arms 57 and legs 61 of the patient.

Figure 2:
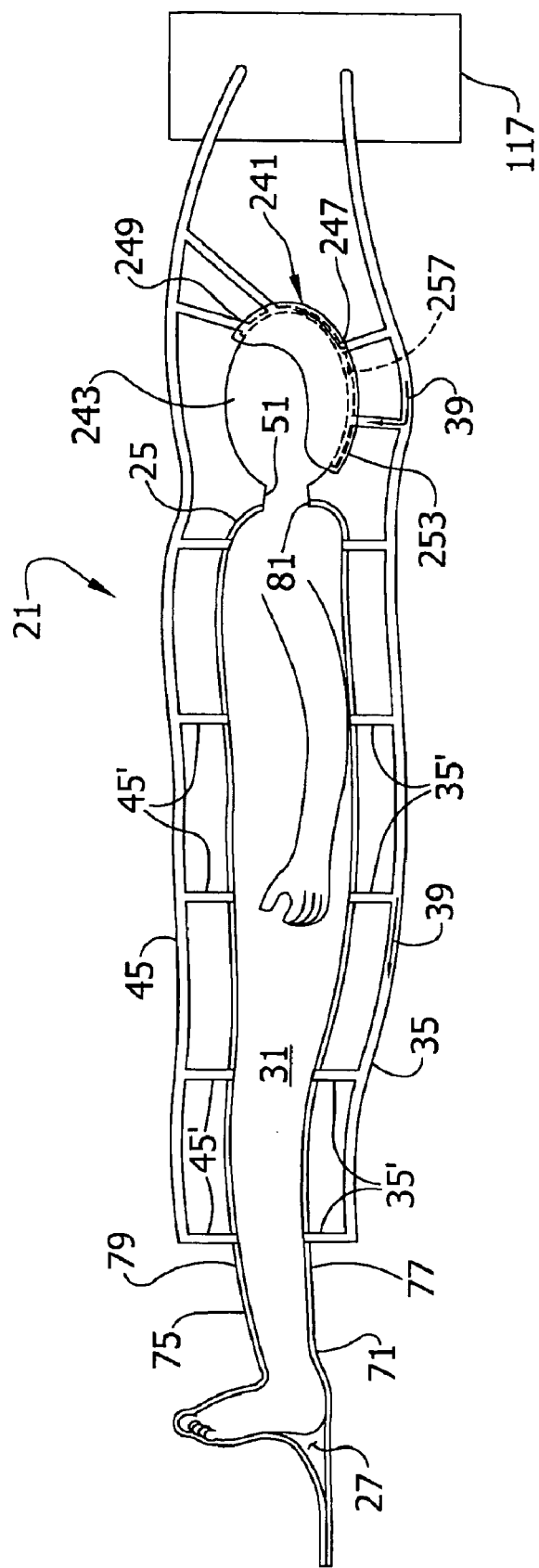
FIG. 2 is a partial elevation of the apparatus of FIG. 1 with portions of the enclosure removed to show detail.

In one embodiment, shown in FIG. 2, the enclosure 25 comprises a first sheet member 71 and a second sheet member 75 in sealing engagement with one another generally at their respective edge margins to form the interior space 27 for receiving the body portion 31. Here, the inlet 35 extends through the first sheet member 71 and the outlet 45 extends through the second sheet member 75. The sheet members 71, 75 are disposed respectively above and below the body portion 31 of the patient, thereby arranging the inlet 35 and the outlet 45 on opposite sides of the patient. As shown in FIG. 2, the inlet 35 and outlet 45 may comprise multiple sub-inlets 35' and sub-outlets 45'. These sub-inlets and sub-outlets facilitate the flow of heat transfer liquid 39 over a larger area of the enclosed portion 31 of the patient's body, thereby promoting increased contact between the liquid and the portion of the patient's body.

More specifically, the first sheet member 71 may comprise a lower member 77 for placement beneath the body portion 31 and the second sheet member 75 may comprise an upper member 79 for placement above the body portion. The enclosure 25 of FIG. 2 depicts such a configuration, and is shown for illustrative purposes only. It is contemplated, for instance, that the outlet 45 may extend through the first sheet member 71, or lower member 77, while the inlet 35 may extend through the second sheet member 75, or upper member 79 (not shown). In the configuration depicted in FIG. 2, where the inlet 35 lies below the outlet 45, air trapped within the interior space 27 of the enclosure 25 will move up toward the outlet and be purged from the enclosure via the outlet. Purging air from the enclosure 25 increases the liquid contact with the body portion 31, thereby promoting more heat transfer between the body portion and liquid 39 for better control of body temperature. The first sheet member 71 and the second sheet member 75 of the illustrated embodiment additionally cooperate to form at least one neck opening 81 in the enclosure 25 (FIG. 2). The neck opening 81 is preferably sized and shaped for sealing engagement of the sheet members 71, 75 with the neck 51 of the patient at the opening. The enclosure 25 may include a strap, a hook and loop fastener or other sealing device (not shown) at the neck opening 81 to further promote sealing of the neck opening about the neck 51 of the patient at the opening. Adhesive hydrogels may also be applied to the neck 51 of the patient to further encourage sealing of the enclosure 25 about the patient's neck.

Figure 3:
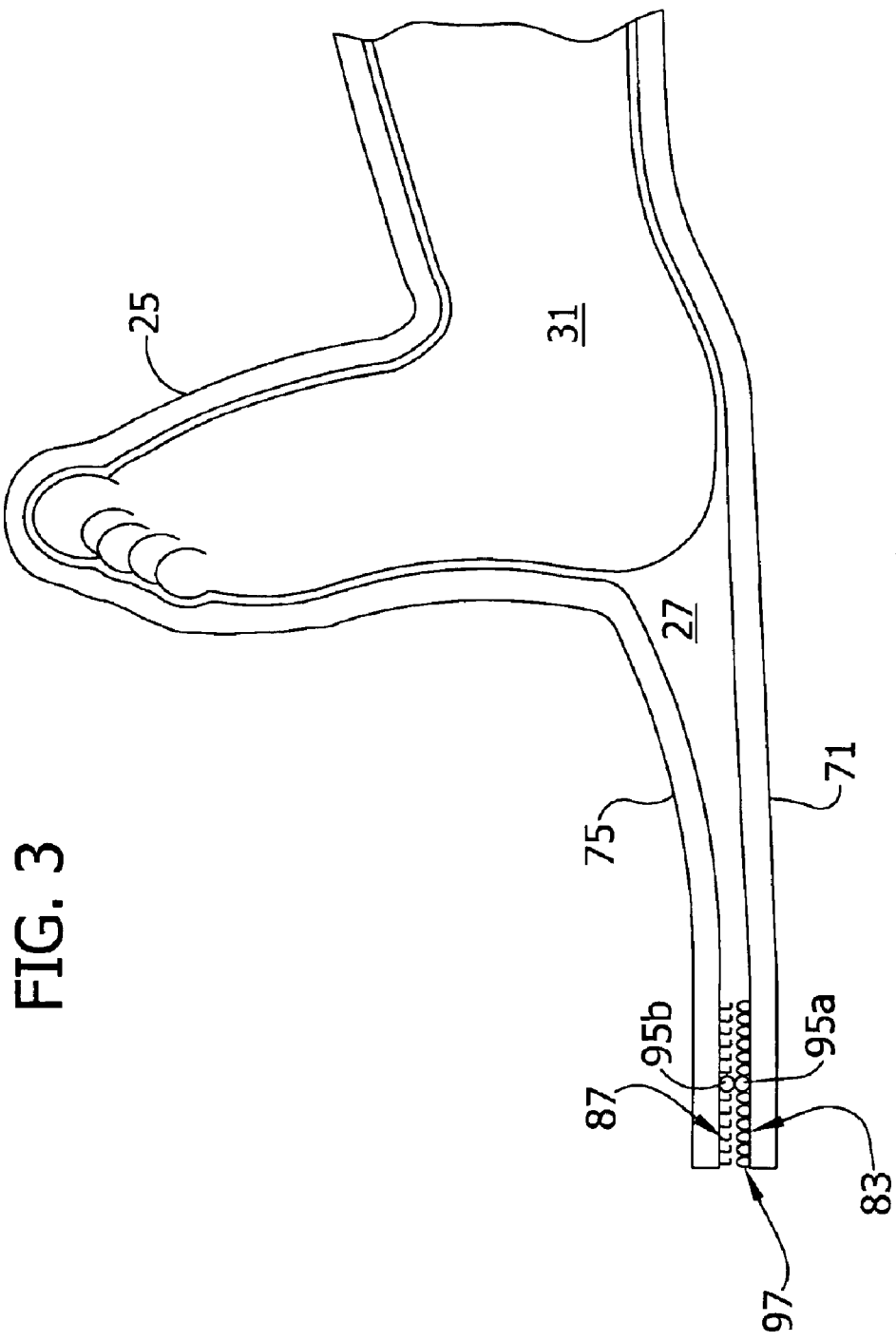
FIG. 3 is an enlarged fragmentary section of the enclosure of FIG. 2.
Figure 4:
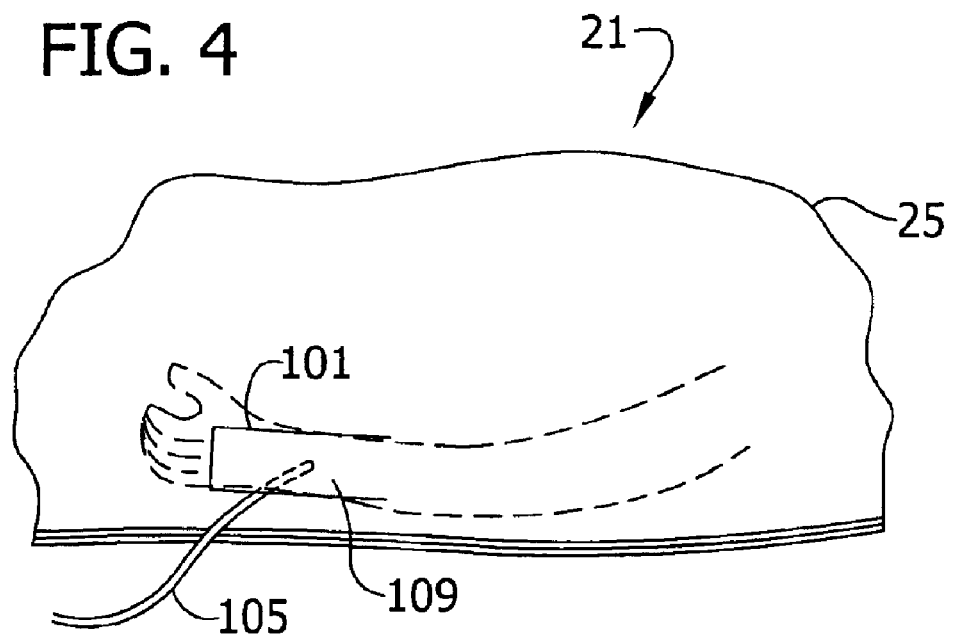
FIG. 4 is a fragmentary elevation of the apparatus with a sealable opening formed by a pivotable flap.

The first sheet member 71 includes a first sealing portion, generally indicated at 83, and the second sheet member 75 includes a second sealing portion, generally indicated at 87 (FIG. 3). The sealing portions 83, 87 are sealingly engageable with one another for sealing the interior space 27 of the enclosure 25. The first and second sealing portions 83, 87 each further comprise a gasket 95, for sealing the first and second sheet members 71, 75, and a hook and loop fastener, generally indicated 97, for holding the sheet members in sealed engagement. The gasket 95 preferably includes a first bead 95a on the first sealing portion 83 and a second bead 95b on the second sealing portion 87. Such beads 95a, 95b may be formed from an elastomeric material, such as rubber. A hook and loop fastener, generally indicated 97, is preferably positioned on opposite lateral sides of the beads 95a, 95b, such that the hook and loop fastener portions compress the beads, forming a sealed enclosure 25. This seal inhibits liquid 39 leakage from the enclosure 25, or a loss of vacuum within the interior space 27 of the enclosure.

Figure 5:
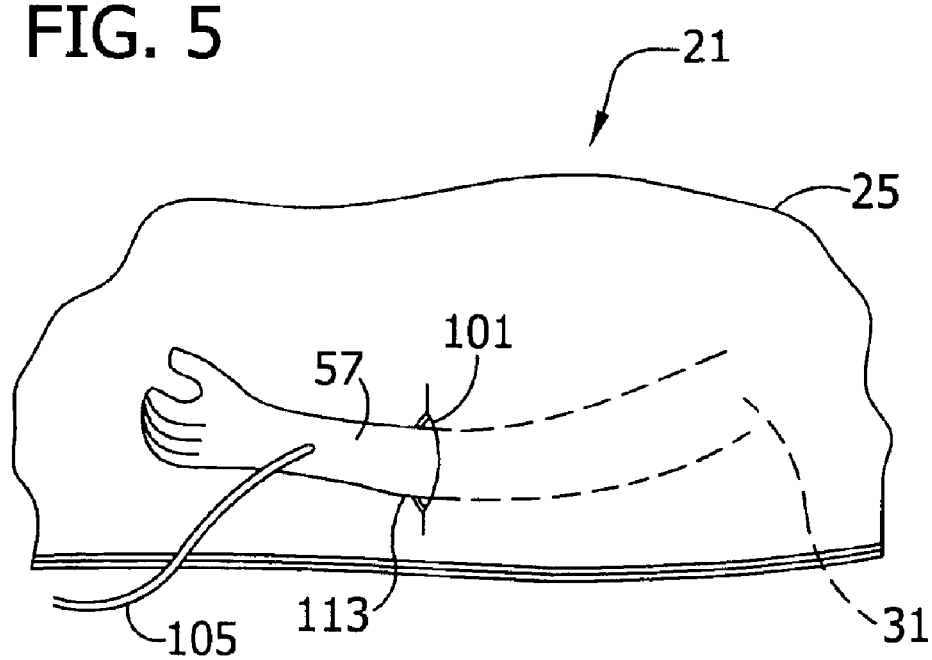
FIG. 5 is a fragmentary elevation of the apparatus with a sealable opening sealed about an arm of the patient.
Figure 6:
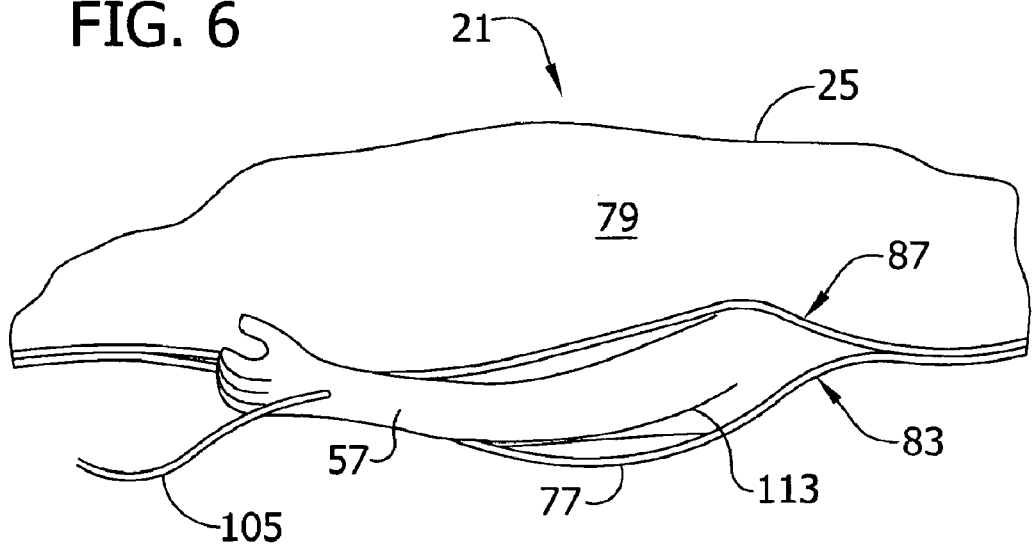
FIG. 6 is a fragmentary elevation of the apparatus with the arm of the patient passing between an upper member and lower member.
Figure 7:
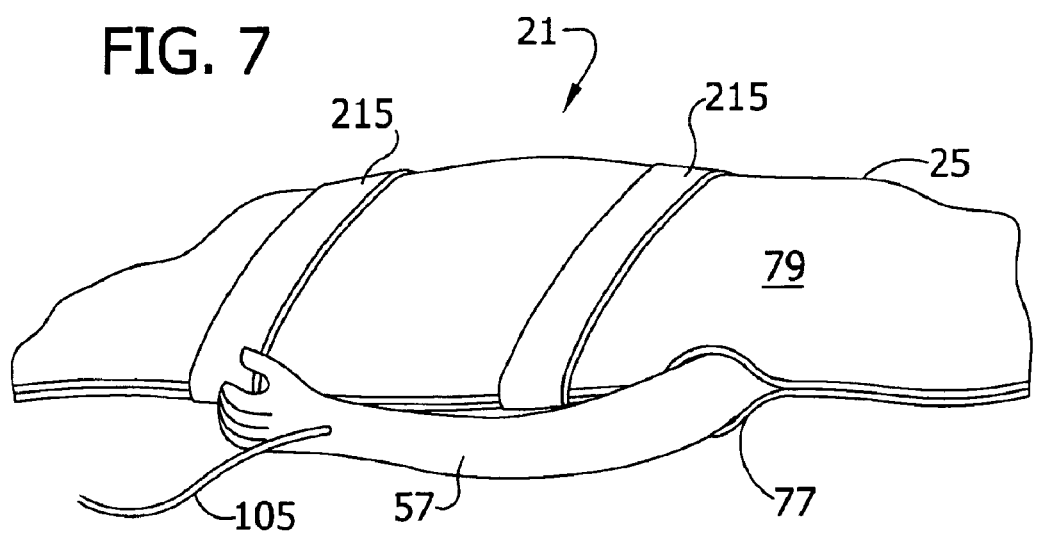
FIG. 7 is a fragmentary elevation of the apparatus of FIG. 6 with the upper and lower members sealed together about the patient's arm.

Referring now to FIGS. 4–7, the enclosure 25 further includes a sealable opening 101 for accessing the interior space 27 of the enclosure. Such a sealable opening 101 may be used for accessing the patient during use of the apparatus 21. The sealable opening 101 may also be sealed about an object, such as medical tubing 105, cords or other items which need to pass through the enclosure 25 into the interior space thereof. In one configuration, depicted in FIG. 4, a pivotable flap 109 defines a closure for the sealable opening 101. Medical tubing 105 or other items may pass through the opening 101 with the flap 109 sealed about them. Moreover, as shown in FIG. 5, the sealable opening 101 may be secured about a second body portion 113 of the patient's body, such as an arm 57 or leg, thereby allowing the second body portion to extend exterior of the enclosure 25 while substantially sealingly enclosing the body portion 31. This is particularly important where access to the second body portion 113 of the patient for performing a medical procedure, such as drawing blood or placing a medical device, e.g., an intravenous catheter, is warranted. As shown in FIGS. 6 and 7, the second body portion 113 may also extend out from the enclosure between the lower member 77 and upper member 79, e.g., without the use of an additional opening 101. In this configuration, the first and second sealing portions 83, 87 cooperate to form a seal about the second body portion 113 as it extends out from the enclosure 25, as shown in FIG. 7. In each of these configurations, adhesive hydrogels may be applied to the second body portion 113 of the patient to further promote sealing of the enclosure 25 about the second body portion.

Figure 8:
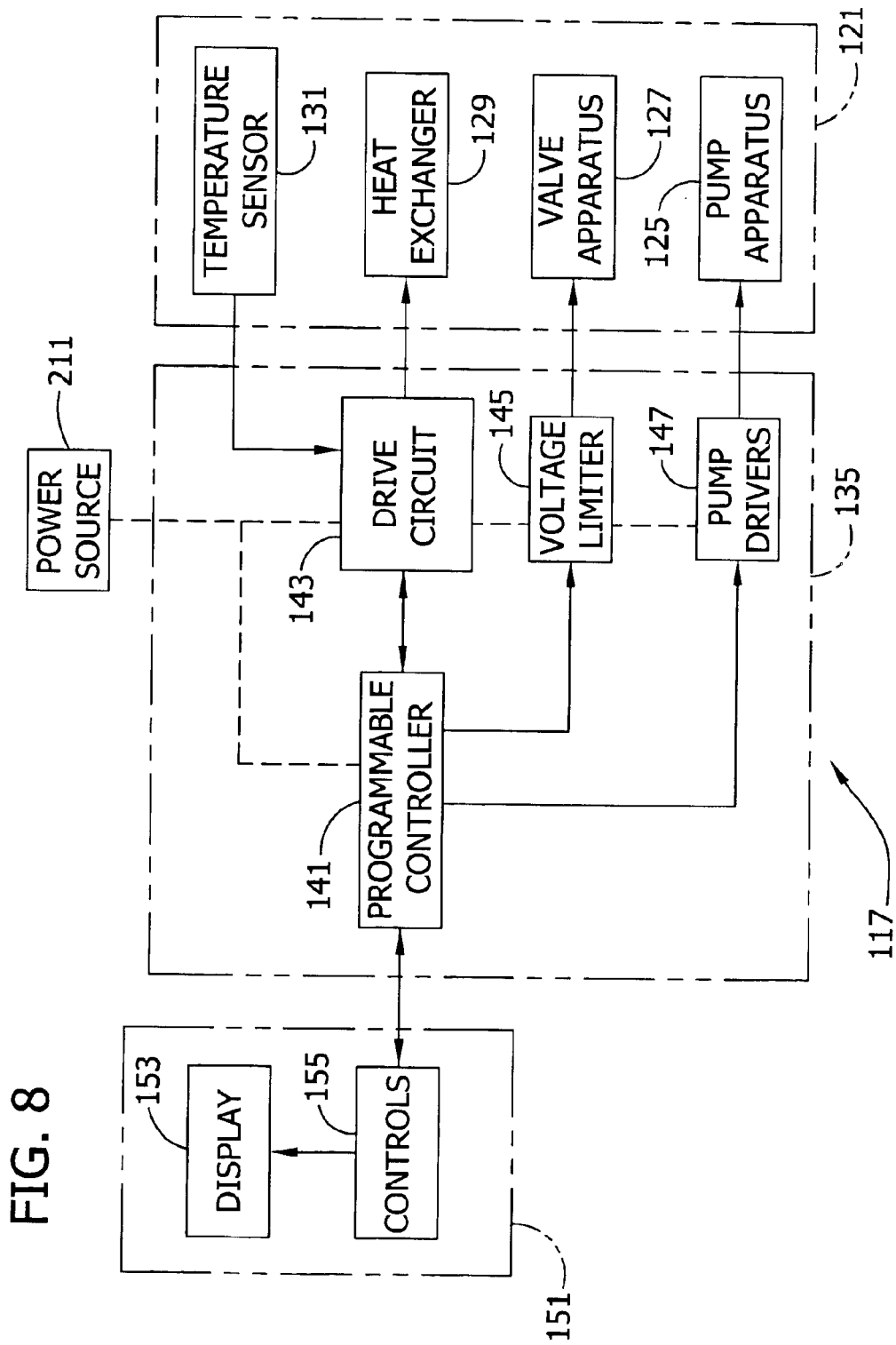
FIG. 8 is a schematic of a portable control unit of the apparatus of the present invention.

Referring now to FIG. 8, the apparatus 21 further comprises a portable control unit, generally indicated at 117, for controlling operation of the apparatus. The control unit 117 comprises a liquid delivery system 121 for directing the heat transfer liquid 39 to flow through the inlet 35 of the enclosure 25 into the interior space 27 to the outlet 45 of the enclosure. The liquid delivery system 121 comprises a pump apparatus 125, a valve apparatus 127, a heat exchanger 129 and a temperature sensor 131. The liquid delivery system 121 is a generally closed, continuous flow system whereby liquid 39 exhausted from the outlet 45 is directed to flow back to the inlet 35 for flow into the interior space 27 of the enclosure 25. A control system 135 communicates with the liquid delivery system 121 to control the flow of liquid 39 through the enclosure 25. The temperature sensor 131 is adapted for sending a body temperature reading of the patient to the control system 135, so that the control system can use this information to control the pump apparatus 125, valve apparatus 127 and heat exchanger 129. The control system 135 comprises a programmable controller 141, an H-bridge drive circuit 143, a voltage limiter 145 and pump drivers 147. The control system 135 provides temperature regulation, drives the pump apparatus 125 and controls the valve apparatus 127. The apparatus 21 further includes a user interface 151 for communicating the status of the system to the user. The user interface 151 includes a display 153 for visually indicating particular parameters of the system and controls 155 that allow the user of the system to selectively control particular system functions. For example, such controls may allow the user to input a set-point, or target, body temperature for the patient. The display 153, for example, could display this set-point temperature along with the actual body temperature of the patient, the liquid 39 temperature and the liquid flowrate, among other things.

Referring back to FIG. 1, the pump apparatus 125 of the portable control unit 117 comprises an outlet pump 161 in fluid communication with the outlet 45 for exhausting heat transfer liquid 39 from the enclosure 25 and an inlet pump 163 in fluid communication with the inlet 35 for pumping heat transfer liquid into the enclosure. The heat exchanger 129 is in fluid communication with the outlet pump 161 and the inlet pump 163, such that liquid 39 exhausted from the enclosure 25 by the outlet pump passes through the heat exchanger before entering the inlet pump. For example, the pumps 161, 163 may be 12 volt direct current pumps having a pumping capacity of 2.4 liters per minute (0.63 gallons per minute). The pumping capacity of such pumps may be increased to 3.0 liters per minute (0.79 gallons per minute) with 18 volts, but not without degrading pump life. Should higher flowrates or other parameters be required, alternative pumps, such as higher capacity gear or centrifugal pumps, may be used without departing from the scope of the present invention.

The pump apparatus 125 further comprises a reservoir 167 in fluid communication with the inlet pump 163 and the heat exchanger 129, such that liquid 39 passing through the heat exchanger flows into the reservoir before flowing into the inlet pump. The relative positions of the reservoir 167 and heat exchanger 129 may also be reversed, such that liquid 39 from the enclosure 25 flows directly into the reservoir for storage, until passing from the reservoir and through the heat exchanger immediately before reentering the enclosure. Such an arrangement might be useful if rapid changes in the liquid 39 temperature were required. Returning now to the original configuration, the reservoir 167 collects liquid 39 at the temperature induced by the heat exchanger 129 and stores it before the inlet pump 163 pumps the liquid into the enclosure 25. The reservoir 167 may be insulated (not shown) to help maintain the temperature of the heat transfer liquid 39 before it is pumped into the enclosure 25. Although any size reservoir may be used, a reservoir having a capacity of about 12 liters (3.2 gallons) is preferable. Even more preferable is a reservoir having a smaller volume, such as 4 liters (1.1 gallons), where such a volume of fluid in the reservoir is sufficient to ensure continued cycling of liquid through the apparatus 21. The reservoir 167 may also comprise a liquid temperature change component 169 in heat transfer communication with the liquid 39 for changing the temperature of the liquid. The component 169 may also provide temperature stabilization once the liquid 39 within the reservoir 167 reaches a particular temperature. In one configuration, the liquid temperature change component 169 contacts the liquid 39 within the reservoir 167. The component 169 may be any material capable of absorbing or releasing heat, such as ice or a phase change material.

The pump apparatus 125 further comprises a bypass conduit 173 in fluid communication with the heat exchanger 129 and the inlet pump 163. The bypass conduit 173 communicates at one end with a first three-way valve 177, between the outlet pump 161 and the heat exchanger 129, and at its other end with a second three-way valve 179, between the inlet pump 163 and the enclosure 25. While operating in a normal mode, without use of the bypass conduit 173, the liquid 39 passes through the outlet pump 161, the first three-way valve 177, the heat exchanger 129, the reservoir 167, the inlet pump 163, the second three-way valve 179 and the enclosure 25. The normal mode is used when a patient is enclosed within the enclosure 25 and liquid 39 is being passed over the body portion 31. In bypass mode, as directed by the user with the controls 155 of the user interface 151 (FIG. 8), the position of the first and second three-way valves 177, 179 switch to divert flow of the liquid 39 from the enclosure 25 to the bypass conduit 173. In addition, the outlet pump 161 is turned off during bypass mode, since liquid bypasses the outlet pump. As a result, liquid 39 flows through the first three-way valve 177, the heat exchanger 129, the reservoir 167, the inlet pump 163, the second three-way valve 179 and the bypass line 173. Bypass mode allows the pump apparatus 125 to control the temperature of the liquid 39, without passing the liquid through the enclosure 25. The bypass mode is particularly useful for pre-cooling or pre-heating the liquid 39 within the reservoir 167. This allows the apparatus 21 to prepare the liquid for use before the patient is placed within the enclosure 25.

In operation, the functioning of the liquid delivery system 121 can control the pressure within the interior space 27 of the enclosure by controlling the movement of liquid 39 through the enclosure 25. For example, where the flowrate of the outlet pump 161 is greater than the flowrate of the inlet pump 163, the flowrate difference will create a negative gage pressure, or vacuum, within the interior space 27 of the enclosure 25. Furthermore, a lower pressure within the interior space 27 of the enclosure 25, relative to the exterior of the enclosure, is beneficial in that it (i) draws the enclosure against the body of the patient to maintain the liquid close to the patient's skin, (ii) minimizes leakage of the enclosure, (iii) encourages blood flow to the skin surface, (iv) minimizes the amount of liquid needed to fill the enclosure and (v) allows the patient's body to be manually compressed or decompressed. Decompression may be readily facilitated by the addition of a hook and loop fastener on the outside of the enclosure 25 (not shown), to which medical personnel could attach a mating decompression tool. The vacuum may be further enhanced by directing the flow of liquid 39 into the bottom of the enclosure 25 and out the top. By requiring the pump to raise the liquid 39 as it passes through the enclosure 25, the pressure drop across the enclosure will increase as flowrates remain constant. Preferably, a vacuum within the enclosure 25 creates a gage pressure within the interior space 27 of between about 0 kiloPascal (0 pounds per square inch) and about −14 kiloPascals (−2.0 pounds per square inch). Alternately, positive gage pressure may be maintained within the enclosure 25, as discussed later herein.

The heat transfer liquid 39 preferably has a temperature less than the temperature of the body portion 31 of the patient so that the liquid cools the body portion of the patient. Preferably, the heat transfer liquid 39 has a temperature in a range of about 1° C. (34° F.) to about 2° C. (36° F.). Such a temperature range provides adequate cooling while minimizing any adverse affects to the skin of the patient. Heat transfer liquid 39 introduced into the enclosure 25 at such a temperature has been found to cool the body at a sufficient rate to induce hypothermia. Examples of hypothermia inducement in animal subjects are described in greater detail below.

Alternately, the enclosure 25 may be used to warm the body portion 31 of the patient within the enclosure if the heat transfer liquid 39 has a temperature greater than the temperature of the portion of the patient's body. One application of such a warming enclosure 25 would be to warm a patient suffering from unintended hypothermia. Preferably, the heat transfer liquid has a temperature in a range of about 43° C. (109° F.) to about 47° C. (117° F.), or more preferably about 45° C. (113° F.).

As described briefly above, the apparatus 21 of the present invention comprises a heat exchanger 129 in fluid communication with the liquid delivery system 121 for altering the temperature of the liquid 39 from an outlet temperature $T_o$, measured after the liquid exits the enclosure 25, to an inlet temperature $T_i$, measured before the liquid enters the enclosure (FIG. 1). After passing through the heat exchanger 129, the liquid 39 may be reintroduced into the enclosure 25 as described above. This allows the same liquid 39 to be used repeatedly between the enclosure 25 and the liquid delivery system 121. Various types of heat exchangers 129 are contemplated as being within the scope of the present invention. For instance, the heat exchanger 129 of the present invention may incorporate a Peltier device or a phase-change material to facilitate returning the liquid 39 to its inlet temperature after passing through the enclosure 25 and being altered by the temperature of the body portion 31 of the patient. Such a heat exchanger 129 requires a flowrate of at least 1.5 liters per minute (0.40 gallons per minute) to maintain adequate efficiency.

Figure 9:
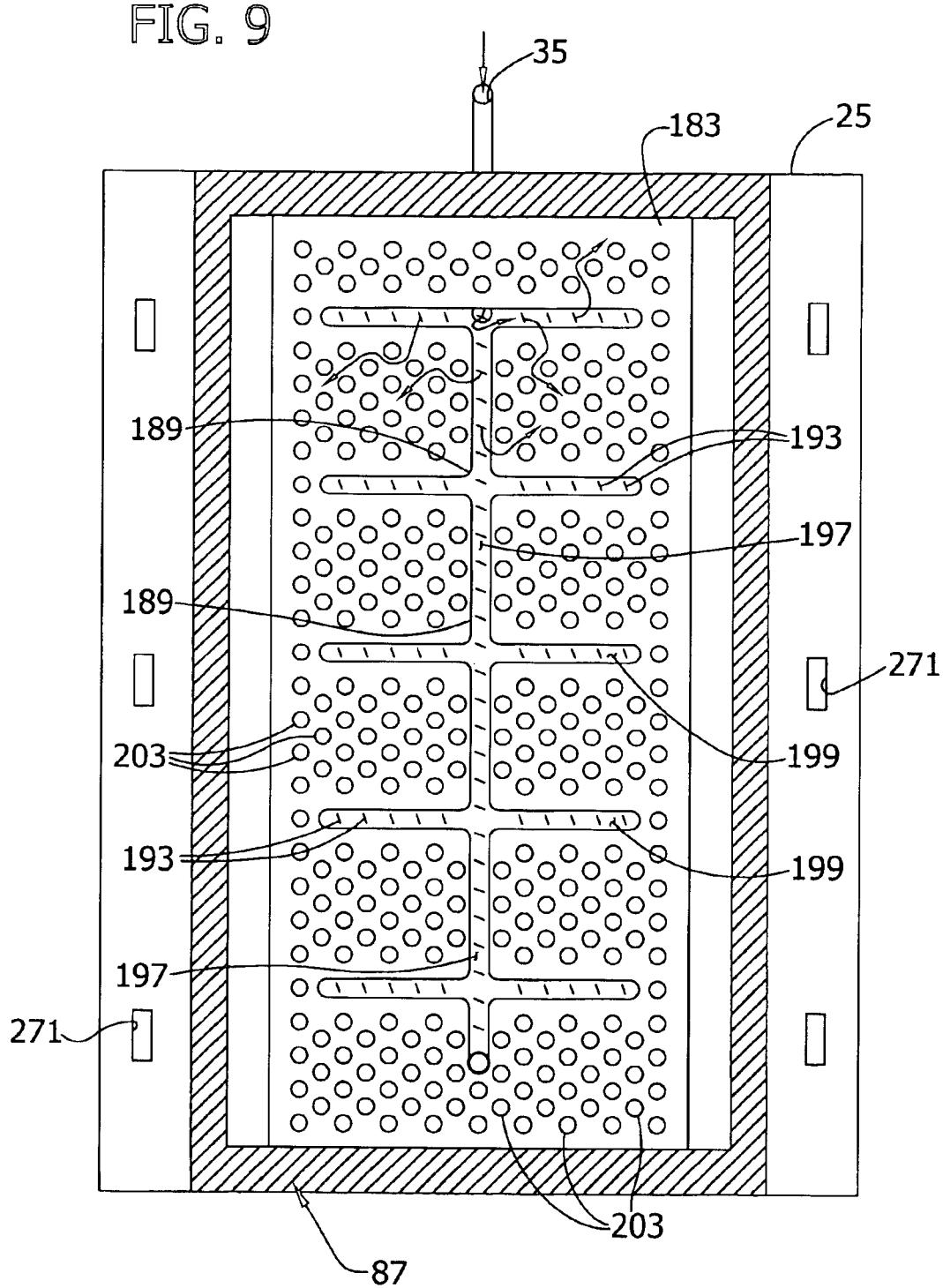
FIG. 9 is a bottom view of the upper member of the apparatus showing liquid passages formed in the apparatus.
Figure 10:
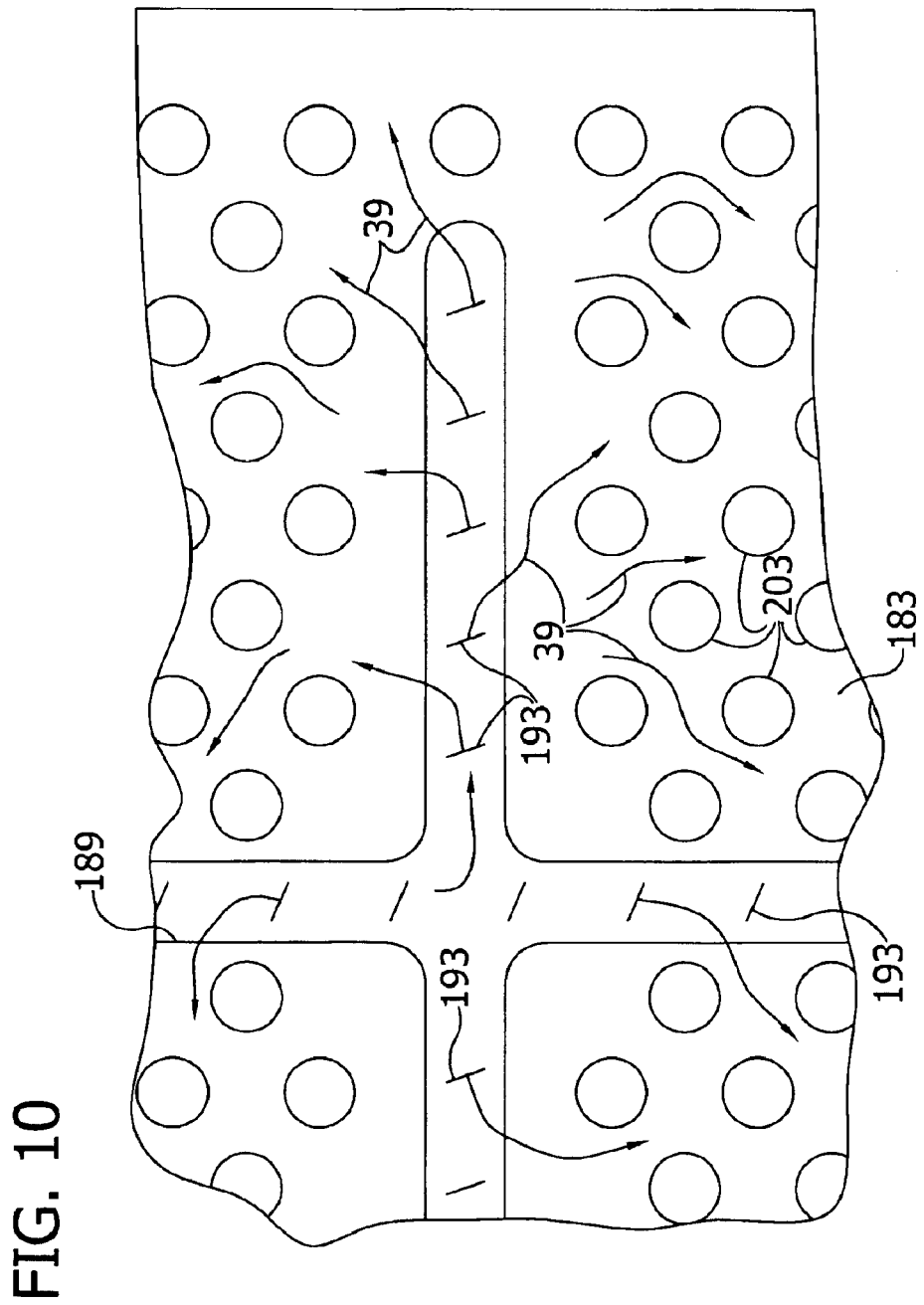
FIG. 10 is an enlarged fragmentary view of the upper member of FIG. 9.
Figure 11:
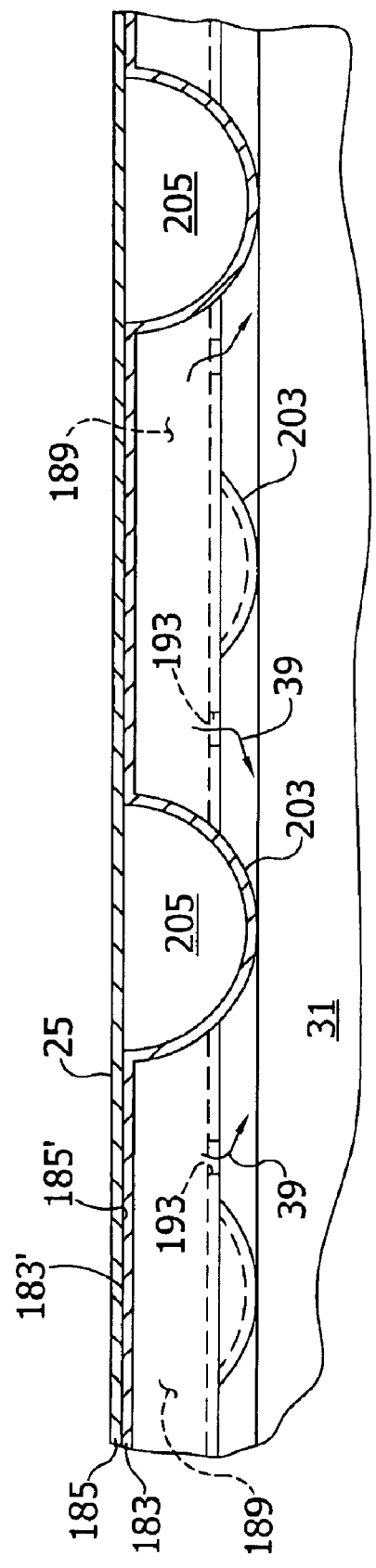
FIG. 11 is a fragmentary side section of the upper member of FIG. 9.

In another embodiment, depicted in FIGS. 9–11, the enclosure 25 comprises a sheet-like body-facing component 183 and a sheet-like outer component 185 that are adapted for face-to-face engagement with one another. The components 183, 185 are joined to one another along their facing sides to form at least one liquid passage 189 between the components. The liquid passage 189 is preferably shaped and sized for fluid communication with the inlet 35 for receiving the heat transfer liquid 39. The body-facing component 183 further has at least one, and preferably several, openings 193 therein corresponding to the liquid passage 189 for allowing the liquid 39 to pass from the liquid passage to between the body-facing component 183 and the portion of the patient's body 31. Before the liquid passage 189 fills with heat transfer liquid 39, the sheet-like body-facing component 183 and sheet-like outer component 185 of the passage lie flat against one another. Once liquid 39 flows inside the passage 189, the cross-sectional area of the passage increases to allow liquid to flow between the components 183, 185. To seal the components together to form the liquid passage 189, heat sealing is preferably used because it provides adequate strength without requiring additional raw materials. Other methods of sealing the components 183, 185 to one another, such as adhesives, are also contemplated as being within the scope of the present invention.

The liquid passage 189 of the present configuration may be further configured to distribute liquid 39 over a larger surface area of the patient's body. For example, the liquid passage 189 may comprise at least one main liquid passage 197 extending longitudinally of the enclosure 25, and at least two secondary liquid passages 199 extending laterally out from the main liquid passage. Preferably, the main liquid passage 197 branches into many secondary liquid passages 199 to further distribute liquid 39 to the patient's body portion 31 within the enclosure 25. The path of these passages may vary without departing from the scope of the present invention.

Figure 12:
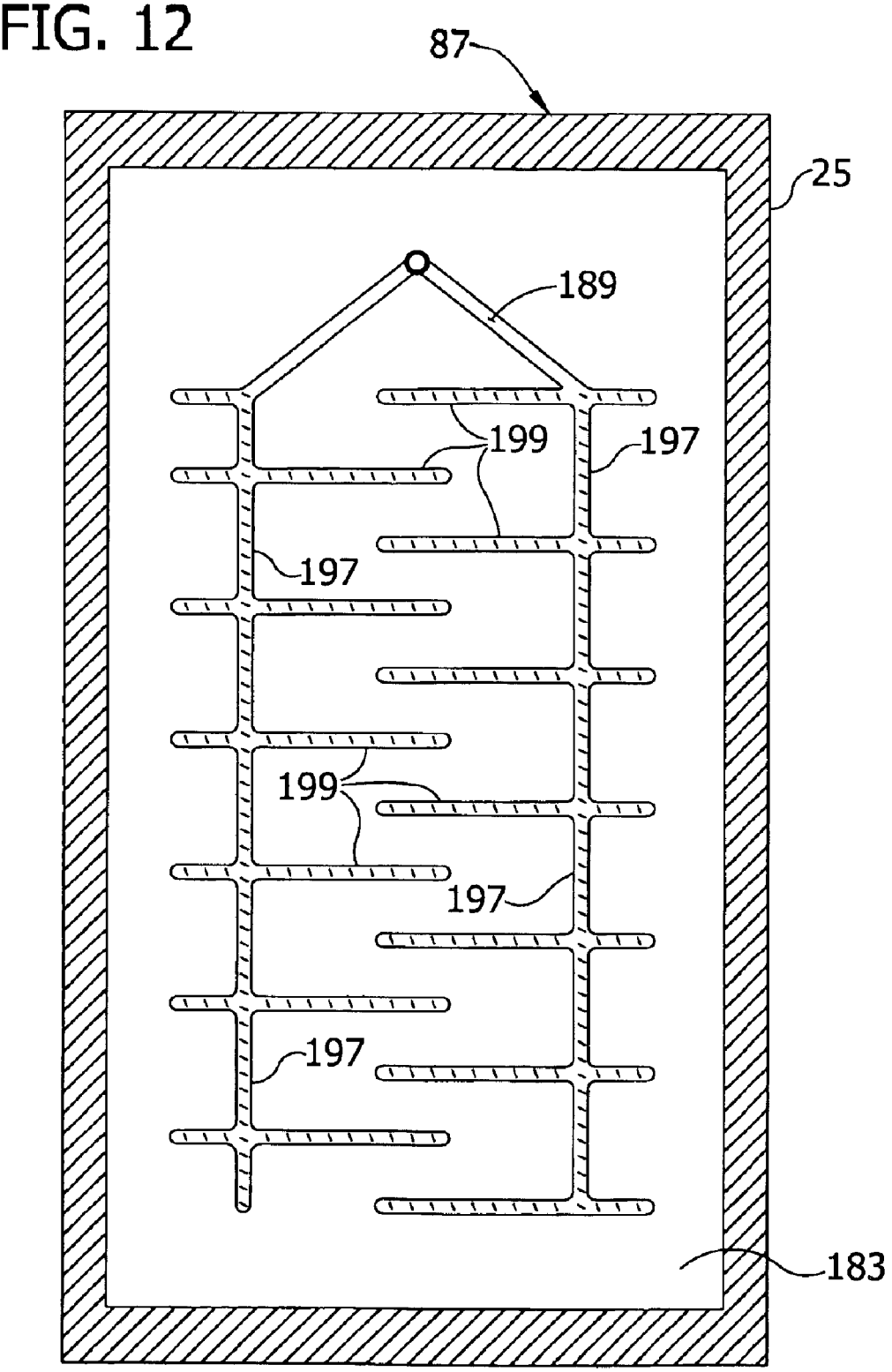
FIG. 12 is a bottom view of a second embodiment of an upper member of the apparatus shown as having liquid passages formed therein.

The components 183, 185 may be joined further along their opposed sides 183', 185' to form gas pockets 203. Such pockets 203 are preferably at least partially filled with gas 205 (e.g., air) such that the pockets act as cushions to engage the body portion 31, holding an adjacent portion of the body-facing component 183 slightly away from the body portion of the patient to increase the interior space 27. As the pockets 203 lift and hold the body-facing component 183 away from the patient's body portion 31, they facilitate liquid 39 movement between the body-facing component and the portion of the patient's body. Because the pockets 203 are rounded, their contact area with the patient's body portion 31 is limited, so that more liquid 39 can contact the skin, thereby increasing the heat transfer effect of the liquid. Where the liquid passages 189 extend abundantly throughout the enclosure 25, air pockets 203 may not be necessary for holding the body-facing component 183 slightly away from the patient's body.

Where the torso 53, arms 57 and legs 61 of the patient are within the interior space 27 of the enclosure 25 (e.g., FIG. 1), the main liquid passages 197 are preferably arranged to engage the patient's torso at a position offset from the medial (e.g., longitudinal center) line of the patient's body, as shown in FIG. 12. This feature is particularly useful where CPR is to be administered to the patient, because chest compressions occur generally along the medial line of the patient. Where the patient is placed within the enclosure 25 and the main liquid passage 197 corresponds approximately with the medial line of the patient, chest compressions may systematically block the flow of liquid 39 through the main liquid passage, thereby reducing liquid flow through the enclosure 25. Where the main liquid passages 197 are offset from the medial line of the patient as shown in FIG. 12, chest compressions performed in rendering CPR treatment are less disruptive of liquid 39 flow through the enclosure 25. Although not shown in FIG. 12, gas pockets 203, as disclosed previously, may be incorporated into the present configuration. Other passage arrangements are also contemplated as being within the scope of the present invention.

A further embodiment of the present invention includes a portable control unit 117 comprising the liquid delivery system 121, a user interface 151, a power source 211 and the control system 135 for powering and controlling the liquid delivery system (FIG. 1). Such a portable control unit 117 would be particularly useful where the apparatus 21 is to be used at a remote site, where electricity is unavailable. Moreover, the self-contained nature of the portable control unit 117 allows it to be carried to the patient, administered to the patient and remain operational while the patient is transported to a medical facility. In one preferred embodiment, the power source 211 is a battery. Other portable power sources, such as engine-based generators and motorized vehicles (e.g., electrical power derived from either) are also contemplated as potential sources of power. In order for the control system 135 to properly control the flow of liquid 39 through the enclosure 25 to control the body temperature of the patient, the temperature sensors 131 of the portable control unit engage the patient's body 31 via wires 133 to monitor the temperature of the patient. Inputs from these temperature sensors 131 feed into the control system 135 for monitoring and controlling the temperature of the patient.

In another embodiment, controlling the liquid delivery system 121 can control the fluid pressure within the enclosure by controlling the flow of liquid 39 through the enclosure 25. For instance, where the flowrate generated by the outlet pump 161 is less than the flowrate generated by the inlet pump 163, the flowrate differential will create a positive gage pressure, e.g., greater than atmospheric pressure, within the interior space 27 of the enclosure 25. Pressurizing the interior space 27 generally applies a compressive force to the patient's body portion 31 as the heat transfer liquid 39 flows over the patient. Preferably, the positive gage pressure within the interior space 27 of between about 0 kiloPascals (0 pounds per square inch) and about 28 kiloPascals (4 pounds per square inch).

However, without restraining the size of the enclosure 25, a positive gage pressure within the interior space 27 would tend to expand the enclosure as more liquid 39 enters the unrestrained enclosure. Thus, several embodiments are contemplated for limiting such outward expansion of the enclosure 25 under positive internal pressure. For example, at least one strap 215 may surround the exterior of the enclosure 25 to inhibit or otherwise limit outward expansion of the enclosure and exerting pressure upon the body portion 31 within the enclosure (e.g., FIG. 8). The strap 215 may further be selectively positionable for engagement with particular portions of the enclosure 25 in contact with particular portions of the patient's body 31 to apply pressure in a particular area. This feature may be particularly useful where the patient is bleeding and pressure upon a specific area may inhibit further bleeding.

Figure 13:
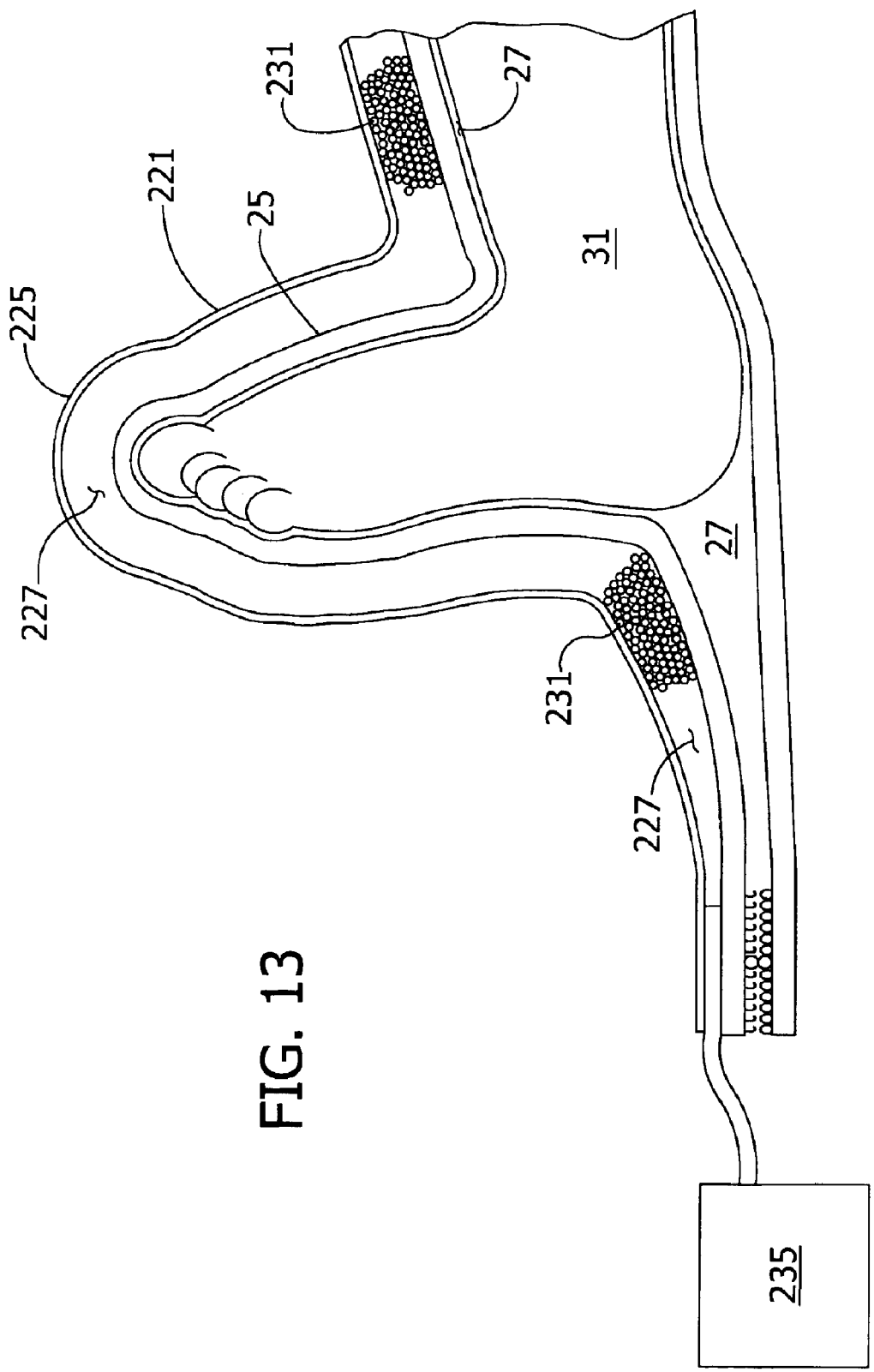
FIG. 13 is a fragmentary section of an apparatus having a jacket with a rigidifiable layer.
Figure 14:
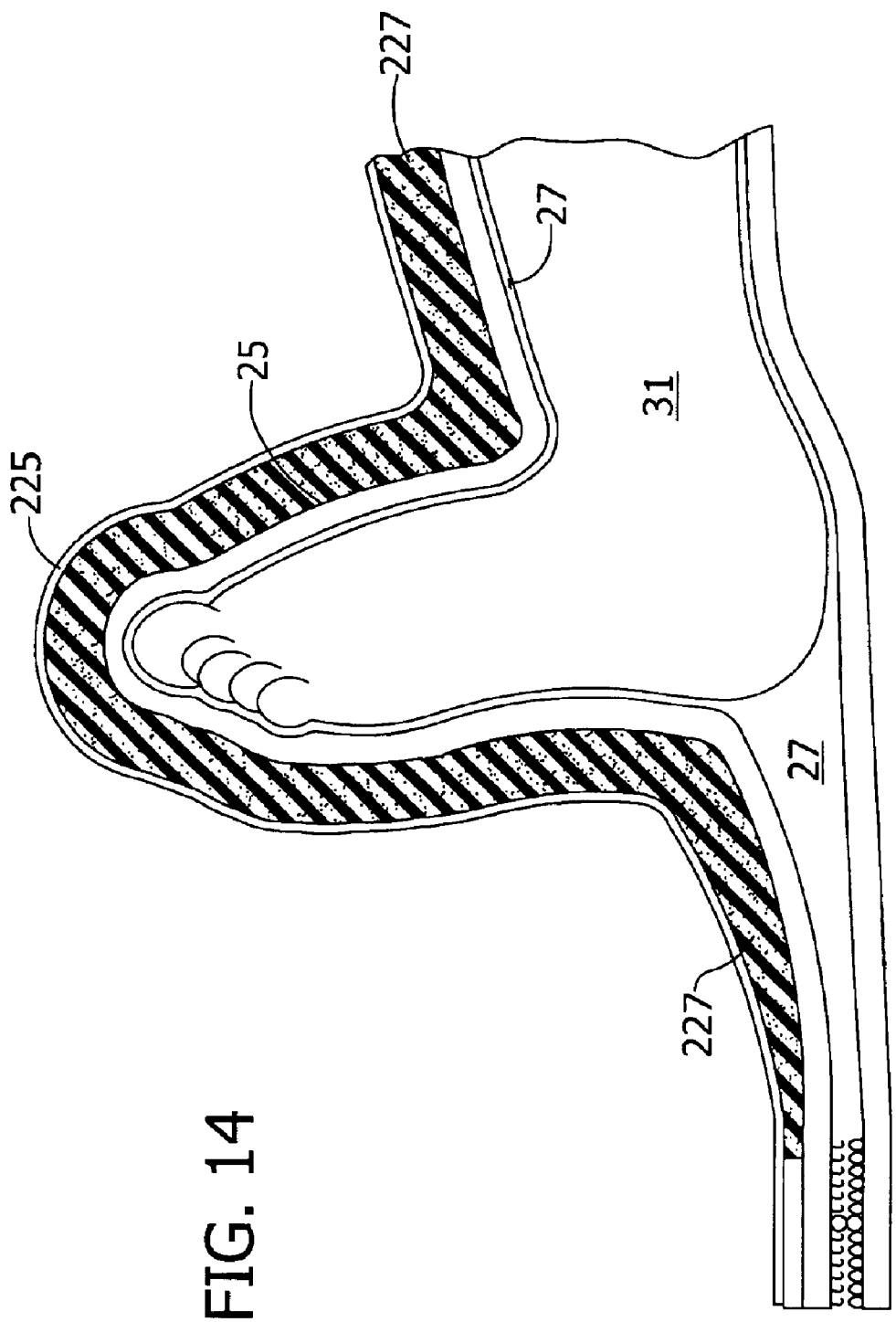
FIG. 14 is a fragmentary section of a second embodiment of apparatus of the present invention having a jacket with a rigidifiable layer.

Referring now to FIGS. 13 and 14, expansion of the enclosure 25 may also be limited by a jacket 221 surrounding the enclosure. The jacket 221 is less elastic than the enclosure 25 and adapted to resist expansion of the enclosure upon pressurizing the interior space 27. The jacket 221 is formed from a material resistant to expansion to thereby generally maintain the shape of the pressurized enclosure 25. For example, a suitable jacket 221 may be constructed from a rigid plastic such as polycarbonate, Acrylonitrile Butadiene Styrene (ABS) or acrylic. This jacket 221 may incorporate reinforcing fibers made of a high tensile strength material such as KEVLAR®, a federally registered mark of E. I. du Pont de Nemours and Company of Wilmington, Del., U.S.A., graphite or glass. Alternately, the jacket 221 may comprise an outer member 225 and a rigidifiable layer 227 between the outer member and the enclosure 25. The rigidifiable layer 227 need not be completely rigid, but is preferably less elastic than the enclosure 25 to limit expansion of the enclosure upon pressurizing the interior space 27. In one configuration, the rigidifiable layer 227 comprises small particulate matter 231, such that the rigidifiable layer may be placed in fluid communication with a vacuum source 235 for removing gas (e.g., air) from between the individual particles of particulate matter, thereby rigidifying the rigidifiable layer between the jacket 221 and enclosure 25 by compacting and densifying the particles with respect to one another (FIG. 13). Once the rigidifiable layer 227 is rigidified, a positive gage pressure may be maintained within the enclosure 25, while limiting further expansion of the enclosure. One suitable particulate matter 231 is polystyrene beads, for example. The rigidifiable layer 227 is shown in FIG. 13 without particulate matter 231 throughout the layer to simplify the figure, although the rigidifiable layer is preferably fully filled with such matter in actual use. Instead of particulate matter, the rigidifiable layer 227 may comprise a polymer capable of starting as a non-solid and solidifying due to a chemical reaction (FIG. 14). For example, a polymer such as two-component, foam-in-place polyurethane may be used to rigidify the rigidifiable layer 227.

Figure 15:
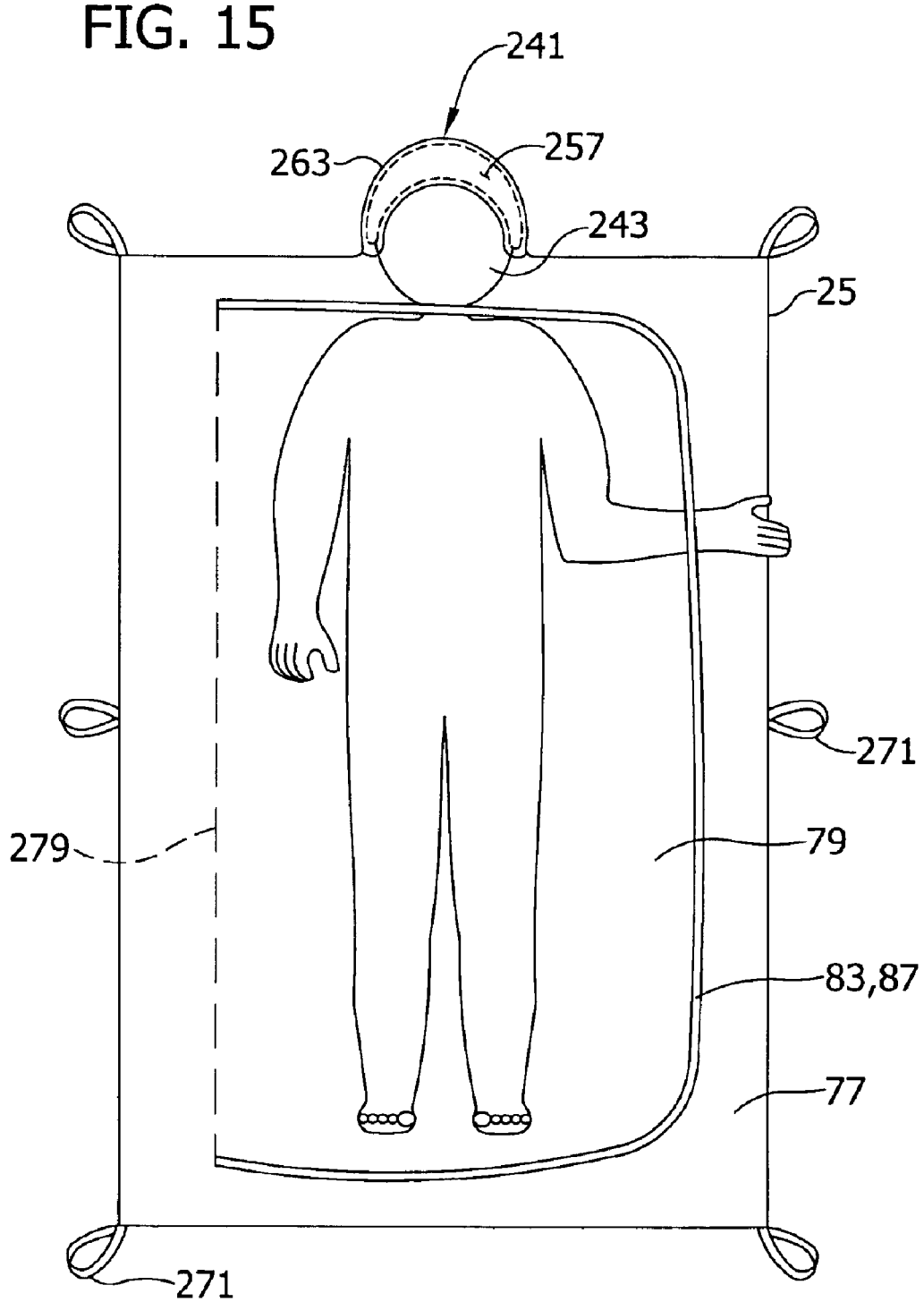
FIG. 15 is a top plan view of a third embodiment of apparatus of the present invention.

With reference to FIG. 15, the apparatus 21 further comprises a head cooling device, generally indicated at 241, engaging the head 243 of the patient for circulating the heat transfer liquid 39 in contact with the head of the patient (FIGS. 1 and 2). The head cooling device 241 further comprises an inlet 247, providing a path for entry of liquid 39 for directly contacting the head 243, and an outlet 249, providing a path for exhausting liquid from the head cooling device. In one embodiment, the head cooling device 241 comprises a helmet 253 for placement upon the head 243 of the patient (FIGS. 1 and 2). The helmet 253 is adapted for sealing engagement with the head 243 of the patient. The helmet 253 is shaped such that the interaction of the helmet and the head 243 form a void 257 so that the heat transfer liquid 39 may flow through the void and contact the head to alter the temperature of the head. In another configuration, the head cooling device 241 comprises a hood 263 attached to the enclosure 25 and wrapping about the head 243 of the patient (FIG. 15). The hood 263 also cooperates with the head 243 to form a void 257 between the hood and the head, thereby allowing the heat transfer liquid 39 to contact the patient's head.

In addition to the head cooling device 241, a mask 267 is adapted for placement over the face of the patient to deliver air to the mouth or nose of the patient via tubing 269 (FIG. 1). The mask 267 may deliver ambient air or oxygen to the patient, as would a conventional breathing mask, or the air delivered through the mask may be at a temperature different than the temperature of the patient's body to aid in cooling or warming the patient.

Additionally, at least a portion of the upper member 79, and preferably the entire upper member, may be transparent for viewing the body portion 31 within the enclosure 25. For instance, a sheet-like body-facing component and sheet-like outer component (as described above) may be formed from a transparent material, such as PVC (polyvinyl chloride), polyethylene or polyurethane.

Referring now to FIGS. 9 and 15, the enclosure 25 may further comprise handles 271 for lifting the enclosure with the body portion 31 received within the enclosure. Such handles 271 may be attachable to the enclosure 25 or formed integrally with the enclosure. For instance, handles 271 may be formed integrally with the lower member, as shown in FIG. 9. Handles 271 provide ease of movement of the enclosure 25, allowing the patient and enclosure to be easily lifted and moved to another location, while heat transfer liquid 39 continues to flow through the enclosure for altering the temperature of the patient.

In another embodiment, depicted in FIG. 15, the upper member 79 is hinged to the lower member 77 along an edge 279 of the upper member. This ensures that the upper member 79 and lower member 77 remain attached and properly aligned for use with respect to one another. In this configuration, the upper member 79 is slightly smaller than the lower member 77. This allows the sealing portions 83,87 of the enclosure 25 to lie laterally inward from the peripheral edge of the lower member 77 of the enclosure.

Figure 16:
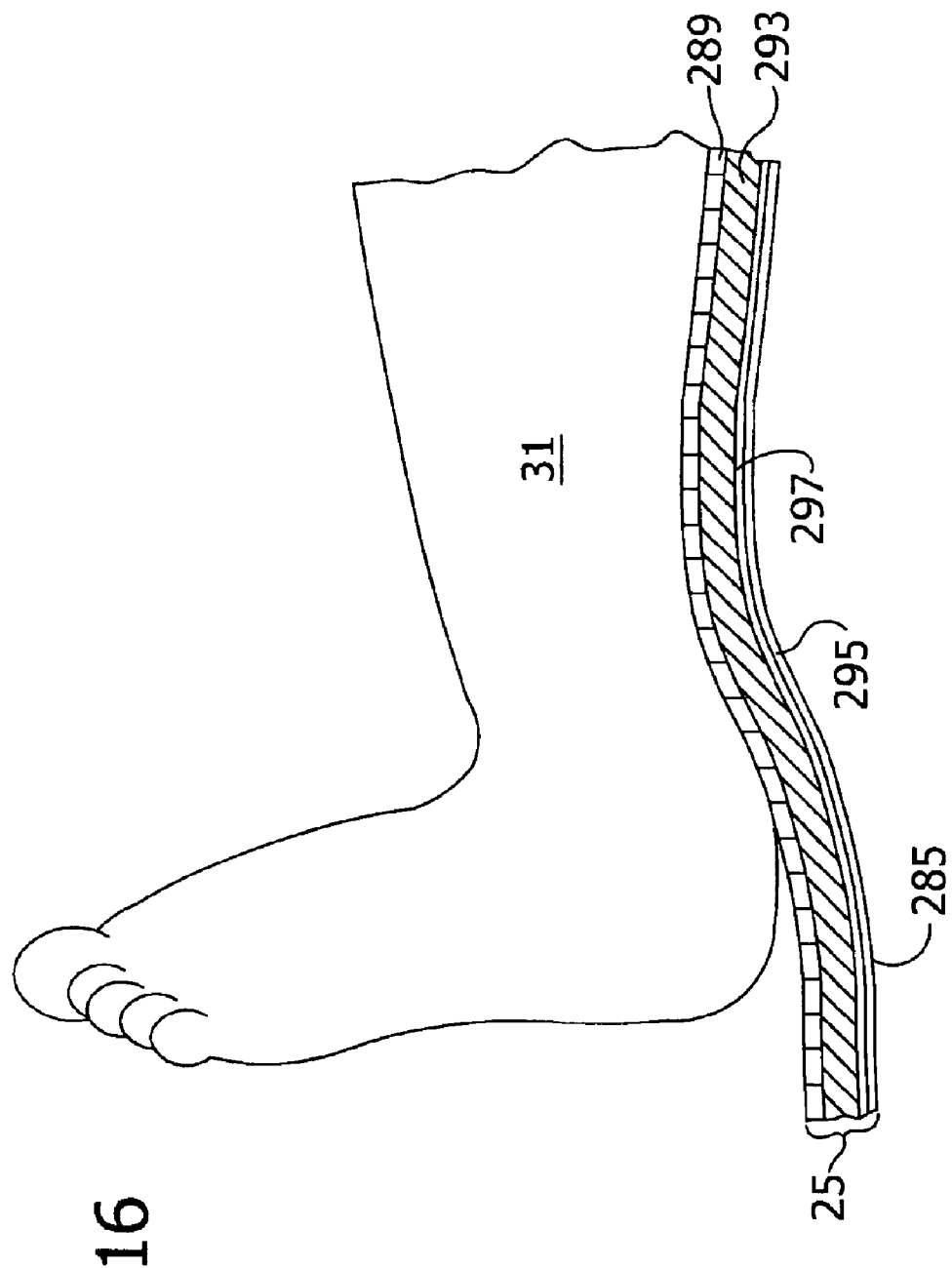
FIG. 16 is an enlarged fragmentary elevation of the enclosure of FIG. 2.

Referring now to FIG. 16, the enclosure 25 of the present invention preferably comprises a liquid impermeable outer layer 285, a mesh body-facing layer 289 and a layer of batting 293 between the outer layer and the body-facing layer. The liquid impermeable outer layer 285 retains the heat transfer liquid 39 within the enclosure 25, while the porous batting layer 293 allows liquid to pass from the batting into contact with the patient's body portion 31 for flow across the skin throughout the enclosure. The mesh layer 289 holds the batting layer 293 in place, allowing substantial contact between the body portion 31 and the liquid 39 within the batting. In one configuration, the liquid impermeable outer layer 285 further comprises a neoprene outer shell 295 with an inner layer 297 of aluminum laminated polyester. The outer shell 295 of neoprene repels liquid, while the inner layer 297 helps insulate the enclosure 25. Preferably, outer shell 295 comprises about 3.2 mm (0.125 inch) to about 1.6 mm (0.0625 inch) thick Neoprene, which is commercially available from John R. Sweet Co. of Mustoe, Va., USA. The inner layer 297 preferably comprises Aluminum Laminated Polyethylene, which is commercially available from Wal-Mart Stores, Inc. of Bentonville, Ark., USA. The middle layer of batting 293 preferably comprises polyester batting, and the mesh layer 289 comprises a nylon screen. For example, the layer of batting 293 may be low loft polyester batting, such as is available from Carpenter Co. of Taylor, Tex., USA. The mesh layer 289 preferably is a Nylon screen mesh, such as is available from McMaster-Carr Supply Company of New Brunswick, N.J., USA. Because each of these components is relatively thin, the enclosure 25 may be folded or rolled into a compact shape for ease of storage. The total thickness of each member 77,79 of the enclosure is preferably less than about 5 mm (0.2 inch).

In one embodiment of a method of the present invention for controlling the body temperature of a patient, at least a portion 31 of the patient's body substantially sealingly enclosed within the interior space 27 of an enclosure 25. The enclosure 25 is generally contiguous with the portion 31 of the patient's body. The method further comprises directing a heat transfer liquid 39 to flow within the interior space 27 in direct liquid contact with the patient's body to promote heat transfer between the heat transfer liquid and the patient's body. Specifically, the method comprises directing the heat transfer liquid 39 to flow from an inlet 35 of the enclosure 25 through the interior space 27 of the enclosure to an outlet 45 thereof. The method may further comprise maintaining heat transfer liquid 39 in contact with the patient's body within the interior space 27 between the enclosure inlet 35 and the enclosure outlet 45. Such a method may also comprise positioning the patient's body generally within the interior space 27 between the enclosure inlet 35 and the enclosure outlet 45, such that the enclosure inlet and enclosure outlet are disposed on generally opposite sides of the patient's body. In addition, the step of directing heat transfer liquid 39 to flow through the interior space 27 of the enclosure 25 may comprise generating a vacuum within the interior space of the enclosure. The method may further comprise the step of applying a compressive force to the patient's body as heat transfer liquid 39 is directed to flow through the interior space 27 of the enclosure 25.

The method may further comprise the step of performing CPR upon the patient simultaneous with the directing step described above. With prior systems for cooling or heating the patient's body, cooling and heating had to be temporarily stopped during resuscitation. With the method of the present invention, CPR does not interfere with the heating or cooling of the patient.

In still another embodiment, a method for controlling the body temperature of a patient comprises the steps of enclosing at least a portion of the patient's body within the interior space 27 of an enclosure 25 with the enclosure being generally contiguous with at least opposite sides of the portion 31 of the patient's body. The method further comprises directing a heat transfer liquid 39 to flow within the interior space 27 in direct liquid contact with at least the opposite sides of the portion of the patient's body to promote heat transfer between the heat transfer liquid and the patient's body.

To examine the process of induced hypothermia in a quantifiable manner, a series of preliminary experiments were conducted using an acute animal preparation. A description of such experiments follows.

EXAMPLE 1

Swine Packed in Ice

The first example studied the effect of total encasement of an animal, here a swine, in ice. This study was conducted in view of recent clinical reports suggesting that cooling gel packs work reasonably well. The study was done by placement of approximately 45 kg (100 pounds) of ice in 2.3 kg (5 pound) plastic bags both under and around the swine. Swine body temperatures and vital signs were then monitored over time, and the ice was removed when the observed core body temperature had dropped from about 34.5° C. (94.1° F.) to about 28.8° C. (83.8° F.).

More specifically, a first swine having a mass of 36 kg (79 pounds) was anaesthetized with Telazol®, a federally registered mark of A.H. Robins Co. of Richmond, Va., U.S.A., and zylazine. The hair of the swine was also clipped. The swine was then instrumented with an electrocardiogram (ECG) via conventional pads for electrically monitoring its heart rhythm during the experiment and a respirator for maintaining proper ventilation. A pulmonary artery catheter was placed via the jugular vein for monitoring the pulmonary artery pressure and blood temperature within the artery. Catheter placement was confirmed by visualizing right ventricular and subsequently pulmonary artery pressure while advancing the catheter. A thermistor sensor of the catheter was connected to a temperature monitor and calibrated in advance, which was then used to calibrate two other type T thermocouples. The first type T thermocouple was connected to the swine's skin under the right front leg with adhesive tape. The second thermocouple was placed deep within the uppermost ear of the swine and then sealed with foam insulation. All sensors were connected to a DATAQ A/D converter system (available from DATAQ Instruments, Inc. of Akron, Ohio, USA) and digitized during the experiments at a rate of 120 Hertz. Once anaesthetized and lying on its side, the exposed exterior of the swine was packed with conventional 2.3 kilogram (5 pound) bags of ice. Approximately 20 bags were used in the experiment, such that a bag of ice was contacting the majority of the skin of the swine.

Figure 17:
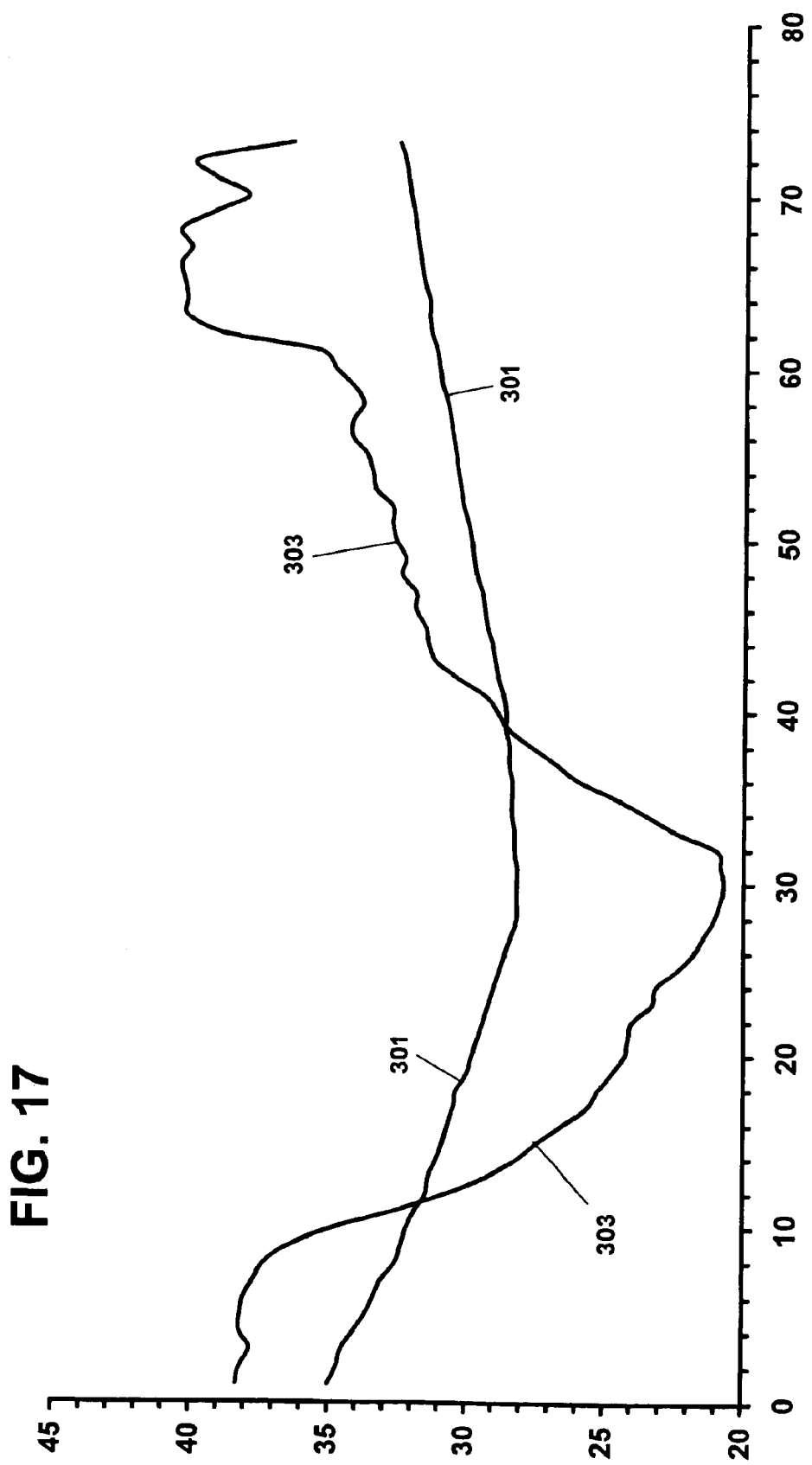
FIG. 17 is a graph depicting the skin temperature and internal body temperature of a swine undergoing the method of the present invention.

The skin temperature and pulmonary artery blood temperature were then recorded over time to determine the cooling rate of the swine due to being packed in ice. The temperature results of this example are depicted in FIG. 17 as curves 301 and 303. For FIGS. 17 and 18, the vertical axis of the chart indicates temperature in Celsius, while the horizontal axis indicates time in minutes. The maximum and minimum values shown on the temperature scales vary between figures. Curve 301 indicates the pulmonary artery temperature of the swine and curve 303 represents the skin temperature. As would be expected, the skin temperature of the swine leads the pulmonary artery temperature, as the skin is providing the cooling for the entire body. Curve 301 demonstrates that eight minutes into the cooling process, the core body temperature of the swine dropped by 1° C. (1.8° F.). After eleven, seventeen and twenty-five minutes, the core temperature had dropped by a total of 2° C. (3.6° F.), 3° C. (5.4° F. ) and 4° C. (7.2° F.), respectively.

EXAMPLE 2

Swine in Enclosure with Liquid Flow

In the second example, a second swine was enclosed in a prototype enclosure of apparatus of the present invention, generally as described above. The apparatus was used to cool and re-warm the animal several times over a period of several hours. The enclosure was operated in one of two ways, with water, as the heat transfer liquid, flowing from the top to the bottom of the enclosure or with water flowing oppositely, bottom to top. Pumping water into the interior space at the top of the enclosure and then out of the interior space at the bottom generated a positive gage pressure within the interior space of the enclosure. Pumping water into the interior space at the bottom of the enclosure and then out of the interior space at the top of the enclosure generated a sub-atmospheric pressure, or partial vacuum, within the interior space of the enclosure. In this mode, the enclosure becomes more conformal to the body and allows for a smaller amount of circulating water as described above.

In this example, a second swine having a mass of 36 kg (79 pounds) was anaesthetized, hairs clipped, instrumented and laid on its side similar to the first swine described above. The swine was then placed within an enclosure sized and shaped for a swine, but substantially as described above. The enclosure was designed to achieve direct liquid contact with the swine's skin. The enclosure included a lower member placed beneath the swine and an upper member placed over the swine. Only the snout of the swine extended out through an opening in the enclosure, allowing the swine to breathe. The lower member and upper member were joined about first and second sealing portions located generally at the edge margin of each member, generally as described above. The enclosure was sealed around the snout of the swine so that a negative gage pressure could be generated within the interior space of the enclosure. The upper and lower members each additionally included five sub-inlets and five sub-outlets, respectively, for circulating water throughout the interior space of the enclosure. The enclosure was fabricated from layers of neoprene, aluminized polyester, polyester batting and nylon mesh, generally as set forth above.

Cooling or warming water was then pumped by computer-controlled diaphragm pumps from reservoirs located near the swine into the enclosure. The pumps used were capable of moving 1.7 liters (0.45 gallon) per minute. As described above, the enclosure dispersed the liquid within the interior space around, over and under the animal in direct contact therewith. The heat exchange system of this example utilized an ice bath reservoir pumped through the enclosure for cooling. The ice bath kept the inlet temperature of the water at about 1 to 2° C. (34 to 36° F.). For the re-warming portion of the experiment, hot water was applied to the swine at an inlet temperature of 45° C. (113° F.).

The skin temperature and pulmonary artery blood temperature were then both recorded over time to determine the cooling rate of the swine. The temperature results of this experiment are depicted in FIG. 18 as curves 305, 307 and 309. Curve 305 indicates the pulmonary artery temperature of the swine packed in ice from example 1, curve 307 indicates the pulmonary artery temperature of the swine in the enclosure with water moving from bottom to top and curve 309 indicates the pulmonary artery temperature of the swine in the enclosure with water moving from top to bottom.

Reviewing curve 307, which pertains to bottom to top water flow, the core body temperature of the swine as measured by the pulmonary artery catheter dropped by 1° C. (1.8° F.) in the first four minutes of the cooling process. Such cooling is twice as fast as the swine packed in ice. Moreover, after seven, ten and fourteen minutes, the swine's core temperature had fallen by a total of 2° C. (3.6° F.), 3° C. (5.4° F.) and 4° C. (7.2° F.), respectively. This method cooled the swine by 4° C. (7.2° F.) in fourteen minutes, which is 79% faster than the swine packed in ice. Similarly, the enclosure employing top to bottom flow, curve 309, cooled the swine more quickly than example 1. At three, six, eight and twelve minutes after beginning the test, for example, the swine's core temperature had fallen by a total of 1° C. (1.8° F.), 2° C. (3.6° F.), 3° C. (5.4° F. and 4° C.

(7.2° F.), respectively. The top to bottom flow cooled the swine by 4° C. (7.2° F.) in twelve minutes, which is 108% faster than the swine packed in ice.

Comparing this rate to published cooling rates from experiments using cooled air, the cooling rates of the present example are much better. Comparing with the hypothermia research noted above (Sterz F. et al., *Mild Therapeutic Hypothermia to Improve the Neurologic Outcome after Cardiac Arrest*, 346 NEW ENG. J. MED. 549–556 (2002)), where cooled air was the medium selected for cooling body temperature, Sterz notes a 1° C. (1.8° F.), 2° C. (3.6° F.) and 3° C. (5.4° F.) core temperature drop in 4 hours, 6 hours and 10 hours, respectively, on human subjects. Obtaining such cooling rates in a swine in a matter of minutes, indicates much more rapid cooling, even recognizing body mass differences between swines and humans.

The results of these examples are summarized in the following table:

| Cooling Method | Packed Ice [*] | Enclosure, Bottom to Top Cooling [*] | Enclosure, Top to Bottom Cooling [*] | Cooled Air (Sterz) [**] |
|---|---|---|---|---|
| 1 C. ° (1.8 F. °) drop in temperature | 8 minutes | 4 minutes | 3 minutes | 4 hours |
| 2 C. ° (3.6 F. °) drop in temperature | 11 minutes | 7 minutes | 6 minutes | 6 hours |
| 3 C. ° (5.4 F. °) drop in temperature | 17 minutes | 10 minutes | 8 minutes | 10 hours |
| 4 C. ° (7.2 F. °) drop in temperature | 25 minutes | 14 minutes | 12 minutes | — |

[*] 36 Kg Swine
[**] Clinical subjects

To summarize, a 4° C. (7.2° F.) temperature drop can be achieved in a 36 kg (79 pounds) animal with normal circulation in 12 minutes. This is a significantly faster core temperature drop than that achieved by packing the same size animal in ice or in clinical studies with human subjects utilizing cooled air. While the animals of the examples had relatively normal circulation, and were under anesthetic agents, the cooling rates achieved are significant. Such therapeutic cooling has the potential to significantly increase the chances of neurologically intact survival following cardiac arrest. Such therapy may also be effective in the treatment of stroke.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. Apparatus for adjusting the body temperature of a patient, said apparatus comprising:
   an enclosure defining an interior apace for receiving at least a portion of a patient's body therein,
   said enclosure being configured for substantially sealingly enclosing said portion of the patient's body within the interior space,
   said enclosure being generally contiguous with the patient's body,
   said enclosure having an inlet for receiving heat transfer liquid into said interior space for flow over the patient's body in direct liquid contact therewith to promote heat transfer between the patient's body and said heat transfer liquid, and an outlet in fluid communication with the interior space of the enclosure fo exhausting said heat transfer liqxid from the enclosure,
   said enclosure comprising a liquid impermeable outer layer and a layer of batting comprising a body-facing layer,
   said batting layer being capable of carrying said liquid throughout the enclosure.

2. Apparatus as set forth in claim 1 further comprising a liquid delivery system for directing said heat transfer liquid to flow through the inlet of the enclosure into the interior space to the outlet of the enclosure.

3. Apparatus as set forth in claim 2 wherein the liquid delivery system is operable to generate a vacuum within the interior space of the enclosure.

4. Apparatus as set forth in claim 3 wherein said vacuum creates a lower pressure within the interior space of the enclosure, relative to the exterior of the enclosure, which draws the enclosure against the body.

5. Apparatus as set forth in claim 4 wherein the gage pressure within the interior space of the enclosure is between about 0 kilopascal (0 pounds per square inch) and about −14 kiloPasCals (−2.0 pounds per square inch).

6. Apparatus as set forth in claim 2 wherein the liquid delivery system is operable to pressurize the interior space of the enclosure.

7. apparatus as set forth in claim 6 further comprising at least one strap selectively positionable for engagement with particular portions of the enclosure engageable with particular portions of the patient's body to apply pressure in a particular area of the patient's body.

8. Apparatus as set forth in claim 6 wherein the gage pressure within the interior apace of the enclosure is between about 0 kilopascals (0 pounds per square inch) and about 28 kilopascals (4 pounds per square inch).

9. Apparatus as set forth in claim 2 wherein said enclosure comprises at least one liquid passage in fluid communication with said inlet for receiving liquid into said passage, said enclosure having at least one opening therein in fluid communication with the liquid passage for allowing liquid to pass from the liquid passage to between the enclosure and the portion of the patient's body.

10. Apparatus as set forth in claim 2 wherein the liquid delivery system is a generally closed, continuous flow system whereby liquid exhausted from the outlet is directed to flow back to said inlet for flow into the interior space of the enclosure.

11. Apparatus as set forth in ciaim 10 further comprising a heat exchanger in fluid communication with said liquid delivery system for altering the temperature of the liquid from an outlet temperature measured after the liquid exits the enclosure to an inlet temperature measured before the liquid enters the enclosure, so that the liquid may be reintroduced into the enclosure after passing through the heat exchanger.

12. Apparatus as set forth in claim 11 wherein said heat exchanger further comprises a peltier device.

13. Apparatus as set forth in claim 11 wherein said heat exchanger further comprises a phase-change material.

14. Apparatus as set forth in claim 10 further comprising a portable control unit, said portable control unit comprising said liquid delivery system, a power source, a control system and a user interface for powering and controlling said liquid delivery system.

15. Apparatus as set forth in claim 14 wherein said power source is a battery.

16. Apparatus as set forth in claim 14 wherein said liquid delivery system further comprises a temperature sensor for engagement with the patient's body for providing the temperature of the patient to the control system.

17. Apparatus as set forth in claim 14 wherein said user interface further comprises controls for controlling the control system and a display for displaying information.

18. Apparatus as set forth in claim 2 wherein
said liquid delivery system comprises an outlet pump in fluid communication with said outlet for exhausting heat transfer liquid from the enclosure and an inlet pump in fluid communication with said inlet for pumping heat transfer liquid into said enclosure.

19. Apparatus as set forth in claim 18 further comprising a heat exchanger in fluid commuxication with said outlet pump and said inlet pump, such that liquid exhausted from the enclosure by said outlet pump passes through said heat exchanger before entering said inlet pump.

20. Apparatus as set forth in claim 19 further comprising a reservoir in fluid communication with said inlet pump and said heat exchanger, such that liquid passing through said heat exchanger flows into said reservoir before flowing into said inlet pump.

21. Apparatus as set forth in claim 20 further comprising a liquid temperature change component in heat transfer communication with said liquid for changing the temperature of said liquid.

22. Apparatus as set forth in claim 21 wherein said liquid temperature change component contacts said liquid in said reservoir.

23. Apparatus as set forth in claim 22 wherein said liquid temperature change component is ice.

24. Apparatus as set forth in claim 22 wherein said liquid temperature change component is a phase change material.

25. Apparatus as set forth in claim 20 further comprising a bypass conduit in fluid communication with said heat exchanger and said inlet pump, said bypass conduit being connectable by a first three-way valve between said outlet pump and said heat exchanger, and a second three-way valve between said inlet pump and said enclosure, thereby allowing said valves to divert flow from the enclosure to the bypass conduit.

26. Apparatus as set forth in claim 19 further comprising a reservoir in fluid communication with said outlet pump and said heat exchanger, such that liquid passing through maid outlet pump flows into said reservoir before flowing into said heat exchanger.

27. Apparatus as set forth in claim 18 wherein said heat transfer liquid is adapted to adjust the core body temperature of the patient.

28. Apparatus as set forth in claim 1 wherein the enclosure is adapted to generally conform to said portion of the patient's body.

29. Apparatus as set forth in claim 1 wherein the enclosure inlet and the enclosure outlet are disposed on generally opposite sides of the enclosure such that the inlet and outlet are disposed on opposite sides of said portion of the patient's body upon enclosure of the patient's body within the interior space of said enclosure.

30. Apparatus as set forth in claim 1 wherein said enclosure comprises a first sheet member and a second sheet member in sealing engagement with one another to form said interior space for receiving said body portion.

31. Apparatus as set forth in claim 30 wherein said inlet extends through said first sheet member and said outlet extends through maid second sheet member.

32. Apparatus as set forth in claim 31 wherein said first sheet member is a lower member for placement beneath said body portion and said second sheet member is an upper member for placement above said body portion, such that air trapped within the interior space of the enclosure will move up within the enclosure to the outlet for purging from the enclosure, to thereby promote increased liquid contact with the body portion.

33. Apparatus as set forth in claim 32 wherein at least a portion of said upper member is transparent.

34. Apparatus as set forth in claim 32 wherein said upper member is hingedly attached to said lower member along an edge of said upper member.

35. Apparatus as set forth in claim 30 wherein said first sheet member includes a first sealing portion and said second sheet member includes a second sealing portion, said sealing portions being sealingly engageable with one another.

36. Apparatus as set forth in claim 35 wherein said first sheet member and said second sheet member cooperate to form at least one neck opening in the enclosure, said neck opening being sized and shaped for sealing engagement with the neck of the patient.

37. Apparatus as set forth in claim 1 wherein said at least a portion of the body of the patient comprises the body of the patient from the neck of the patient downward, including the torso, arms and legs of the patient.

38. Apparatus as set forth in claim 1 wherein said liquid has a temperature less than the temperature of the portion of the patient's body, such that the liquid cools said body portion of the patient.

39. Apparatus as set forth in claim 38 wherein said liquid temperature is in a range from about 1° C. (34° F.) to about 2° C. (36° F.).

40. Apparatus as set forth in claim 1 wherein said liquid has a temperature greater than the temperature of the portion of the patient's body, such that the liquid warms said body portion of the patient.

41. Apparatus as set forth in claim 40 wherein said liquid temperature is in a range from about 43° C. (109° F.) to about 47° C. (117° F.).

42. Apparatus as set forth in claim 1 wherein said enclosure further comprises handles for lifting said enclosure with said body portion received within said enclosure.

43. Apparatus as set forth in claim 1 wherein said heat transfer liquid in adapted to adjust the core body temperature of the patient.

44. Apparatus for adjusting the body temperature of a patient, said apparatus comprising:
an enclosure defining an interior space for receiving at least a portion of a patient's body therein,
said enclosure being configured for substantially sealingly enclosing said portion of the patient's body within the interior space, said enclosure being generally contiguous with the patient's body, said enclosure having an inlet for receiving heat transfer liquid into said interior space for flow over the patient's body in direct liquid contact therewith to promote heat transfer between the patient's body and said heat transfer liquid, and an outlet in fluid communication with the interior space of the enclosure for exhausting said heat transfer liquid from the enclosure;

a liquid delivery system for directing said heat transfer liquid to flow through the inlet of the enclosure into the interior space to the outlet of the enclosure, the liquid delivery system being operable to pressurize the interior space of the enclosure; and a jacket surrounding said enclosure, said jacket being less elastic than the enclosure and adapted to resist expansion of the enclosure upon pressurizing said interior space of the enclosure.

45. Apparatus as set forth in claim 44 wherein said jacket comprises an outer member and a rigidifiable layer between said outer member and said enclosure.

46. Apparatus as set forth in claim 45 wherein said rigidifiable layer further comprises particulate matter, such that said rigidifiable layer may be placed in fluid ommunication with a vacuum source for removing gas between the individual pieces of particulate matter, thereby rigidifying said rigidifiable layer between the jackcet and enclosure such that a positive gage pressure may be maintained within said enclosure without further expansion of said enclosure.

47. Apparatus as set forth in claim 46 wherein said particulate matter comprises polystyrene beads.

48. Apparatus as set forth in claim 45 wherein waid rigidifiable layer further comprises a polymer capable of solidifying due to a chemical reaction.

49. Apparatus for adjusting the body temperature of a patient, said apparatus comprising:

an enclosure defining an interior space for receiving at least a portion of a patient's body therein, said enclosure being configured for substantially sealingly enclosing said portion of the patient's body within the interior space, said enclosure being generally contiguous with the patient's body, said enclosure having an inlet for receiving heat transfer liquid into said interior space for flow over the patient's body in direct liquid contact therewith to promote heat transfer between the patient's body and said heat transfer liquid, and an outlet in fluid communication with the interior space of the enclosure for exhausting said heat transfer liquid from the enclosure; and a liquid delivery system for directing said heat transfer liquid to flow through the inlet of the enclosure into the interior space to the outlet of the enclosure, wherein said enclosure comprises a sheet-like body-facing component and a sheet-like outer component, said sheet-like body-facing component and sheet-like outer component being adapted for face-to-face engagement with one another, said components further being joined to one another along their facing sides to form at least one liquid passage between the components, said liquid passage being shaped and sized for fluid communication with said inlet for receiving liquid, said body-facing component having at least one opening therein corresponding to the liquid passage for allowing liquid to pass from the liquid passage to between the body-facing component and the portion of the patient's body.

50. Apparatus as set forth in claim 49 wherein said components are further joined along their facing aides to form gas pockets, such pockets being at least partially filled with gas such that the pockets act as cushions to engage the body portion and hold an adjacent portion of the body-facing component away from the body portion of the patient, thereby facilitating liquid movement between the body-facing component and the portion of the patient's body.

51. Apparatus as set forth in claim 49 wherein said liquid passage further comprises at least one main liquid passage and at least two secondary liquid passages extending from said main passage.

52. Apparatus as set forth in claim 51 wherein said at least a portion of the body of the patient comprises the body of the patient from the neck of the patient downward, including the torso, arms and legs of the patient, said main liquid passage being arranged to engage said patient's torso at a position offset from the medial line of the patient's body.

53. Apparatus for adjusting the body temperature of a patient, said apparatus comprising:

an enclosure defining an interior space for receiving at least a portion of a patient's body therein, said enclosure being configured for substantially sealingly enclosing said portion of the patient's body within the interior space, said enclosure being generally contiguous with the patient's body, said enclosure having an inlet for receiving heat transfer liquid into said interior space for flow over the patient's body in direct liquid contact therewith to promote heat transfer between the patients body and said heat transfer liquid, and an outlet in fluid communication with the interior space of the enclosure for exhausting said heat transfer liquid from the enclosure;

wherein said enclosure comprises a first sheet member and a second sheet member in sealing engagement with one another to form said interior space for receiving said body portion, said first sheet member includes a first sealing portion and said second sheet member includes a second sealing portion, said sealing portions being sealingly engageable with one another, said first and second sealing portions comprising a gasket for sealing the first and second sheet members and a hook and loop fastener for holding said sheet members in sealed engagement.

54. Apparatus for adjusting the body temperature of a patient, said apparatus comprising:

an enclosure defining an interior space for receiving a body of a patient from the neck of the patient downward, including the torso, arms and legs of the patient, said enclosure being configured for substantially sealingly enclosing said portion of the patient's body within the interior space, said enclosure being generally contiguous with the patient's body waid enclosure having an inlet for receiving heat transfer liquid into said interior space for flow over the patient's body in direct liquid contact therewith to promote heat transfer between the patient's body and said heat transfer liquid, and an outlet in fluid communication with the interior space of the enclosure for exhausting said heat transfer liquid from the enclosure, said enclosure including a sealable opening for accessing the interior space of the enclosure and a pivotable flap for sealing the sealable opening.

55. Apparatus for adjusting the body temperature of a patient, said apparatus comprising:

an enclosure defining an interior space for receiving a body of a patient from the neck of the patient downward, including the torso, arms and legs of the patient, said enclosure being configured for substantially sealingly enclosing said portion of the patient's body within the interior space, said enclosure being generally contiguous with the patient's body said enclosure having an inlet for receiving heat transfer liquid into said interior space for flow over the patient's body in direct liquid contact therewith to promote heat transfer between the patient's body and said heat transfer liquid, and an outlet in fluid communication with the interior space of the enclosure for exhausting said heat transfer liquid from the enclosure, said enclosure including a sealable opening for accessing the interior space of the enclosure, said sealable opening being adapted to be secured about a second body portion of the patient, thereby allowing said second body portion to extend outside the enclosure while substantially sealingly enclosing the first portion.

56. Apparatus for adjusting the body temperature of a patient, said apparatus comprising:

an enclosure defining an interior space for receiving at least a portion of a patient's body therein, said enclosure being configured for substantially sealingly enclosing said portion of the patient's body within the interior space, said enclosure being generally contiguous with the patient's body, said enclosure having an inlet for receiving heat transfer liquid into said interior space for flow over the patient's body in direct liquid contact therewith to promote heat transfer between the patient's body and said heat transfer liquid, and an outlet in fluid communication with the interior space of the enclosure for exhausting said heat transfer liquid from the enclosure, said enclosure comprising a liquid impermeable outer layer, a mesh body-facing layer and a layer of batting between said outer layer and said body-facing layer, said batting layer being capable of carrying said liquid throughout the enclosure.

57. Apparatus as set forth in claim 56 wherein said liquid impermeable outer layer further comprises a neoprene outer shell with an inner layer of aluminum laminated polyester.

58. Apparatus as set forth in claim 56 wherein said middle layer of batting comprises polyester batting.

59. Apparatus as set forth in claim 56 wherein said mesh layer comprises a nylon screen.

60. Apparatus for adjusting the body temperature of a patient, said apparatus comprising;

an enclosure defining an interior space for receiving at least a portion of a patient's body therein, said enclosure being configured for substantially sealingly enclosing said portion of the patient's body within the interior space, said enclosure being generally contiguous with the patient's body, said enclosure having an inlet for receiving heat transfer liquid into said interior space for flow over the patient's body in direct liquid contact therewith to promote heat transfer between the patient's body and said heat transfer liquid, and an outlet in fluid communication with the interior space of the enclosure for exhausting said heat transfer liquid from the enclosure;

a helmet for engaging the head of the patient for circulating said liquid in contact with the head of the patient, said helmet being adapted for sealing engagement with said head of the patient, the interaction of said helmet and said head forming a void between said helmet and said head such that liquid may flow through the void and contact said head to alter the temperature of said head; and a mask for placement over the face of the patient for delivery of air to the mouth or nose of the patient.

61. Apparatus as set forth in claim 60 wherein said air delivered through said mask is at a temperature different than the temperature of the patient's body.

62. Apparatus as set forth in claim 60 further comprising an inlet through said helmet for providing a path for entry of liquid for directly contacting said head and an outlet through said helmet for providing a path for exit of liquid from the helmet.

63. A method for controlling the body temperature of a patient during a cardiopulmonary resuscitation procedure, said method comprising the steps of:

substantially sealingly enclosing at least a portion of the patient's body within the interior space of an enclosure, the enclosure being generally contiguous with said portion of the patient's body;

directing a heat transfer liquid to flaw within the interior space in direct liquid contact with the patient's body to promote heat transfer between the heat transfer liquid and the patient's body; and performing cardiopulmonary resuscitation upon the patient simultaneous with the directing step.

64. A method as set forth in claim 63 further comprising maintaining heat transfer liquid in contact with the patient's body within the interior space between the enclosure inlet and the enclosure outlet.

65. A method as set forth in claim 64 further comprising positioning the patient's body generally within the interior space between the enclosure inlet and the enclosure outlet such that the enclosure inlet and enclosure outlet are disposed on generally opposite sides of the patient's body.

66. A method as set forth in claim 63 wherein the step of directing heat transfer liquid to flow through the interior space of the enclosure comprises generating a vacuum within the interior space of the enclosure.

67. A method as set forth in claim 66 further comprising the step of applying a compressive force to the patient's body as heat transfer liquid is directed to flow through the interior space of the enclosure in direct liquid contact with the patient's body.

68. A method as set forth in claim 63 further comprising maintaining said heat transfer liquid at a temperature sufficient to control the core body temperature of the patient.

69. Apparatus for adjusting the body temperature of a patient, said apparatus comprising:

an enclosure defining an interior space for receiving at least a portion of a patient's body therein, said enclosure having an inlet for receiving heat transfer liquid into said interior space for flow over the patient's body in direct liquid contact therewith to promote heat transfer between the patient's body and said heat transfer liquid, and an outlet in fluid communication with the interior space of the enclosure for exhausting said heat transfer liquid from the enclosure;

a liquid delivery system for directing said heat transfer liquid to flow through the inlet of the enclosure into the interior space to the outlet of the enclosure, the liquid delivery system being operable to pressurize the interior space of the enclosure; and a jacket surrounding said enclosure, said jacket being less elastic than the enclosure and adapted to resist expansion of the enclosure upon pressurizing said interior space of the enclosure.

70. Apparatus for adjusting the body temperature of a patient, said apparatus comprising:

an enclosure defining an interior space for receiving at least a portion of a patient's body therein, said enclosure having an inlet for receiving heat transfer liquid into said interior space for flow over the patient's body in direct liquid contact therewith to promote heat transfer between the patient's body and said heat transfer liquid, and an outlet in fluid communication with the interior space of the enclosure for exhausting said heat transfer liquid from the enclosure, said enclosure comprising a sheet-like body-facing component and a sheet-like outer component, said sheet-like body-facing component and sheet-like outer component being in relationship face-to-face with one another, said components further being joined to one another to form at least one liquid passage between the components, said liquid passage being shaped and sized for fluid communication with said inlet for receiving liquid, said body-facing component having at least one opening therein corresponding to the liquid passage for allowing liquid to pass from the liquid passage to between the body-facing component and the portion of the patient's body.

71. Apparatus for adjusting the body temperature of a patient, said apparatus comprising:

an enclosure defining an interior space for receiving at least a portion of a patient's body therein, said enclosure being configured for substantially sealingly enclosing said portion of the patient's body within the interior space, said enclosure having an inlet for receiving heat transfer liquid into said interior space for flow over the patient's body in direct liquid contact therewith to promote heat transfer between the patient's body and said heat transfer liquid, and an outlet in fluid communication with the interior space of the enclosure for exhausting said heat transfer liquid from the enclosure;

wherein said enclosure comprises a first sheet member and a second sheet member in sealing engagement with one another to form said interior space for receiving said body portion, said first sheet member including a first sealing portion and said second sheet member includes a second sealing portion, said sealing portions being sealingly engageable with one another, said first and second sealing portions comprising a gasket for sealing the first and second sheet members and a hook and loop fastener for holding said sheet members in sealed engagement.

72. Apparatus for adjusting the body temperature of a patient said apparatus comprising:

an enclosure defining an interior space for receiving at least a portion of a patient's body therein, said enclosure having an inlet for receiving heat transfer liquid into said interior space for flow over the patient's body in direct liquid contact therewith to promote heat transfer between the patient's body and said heat transfer liquid, and an outlet in fluid communication with the interior space of the enclosure for exhausting said heat transfer liquid from the enclosure, said enclosure comprising a liquid impermeable outer layer, a mesh body-facing layer and a porous layer between said outer layer and said body-facing layer, said porous layer being capable of carrying said liquid throughout the enclosure.

73. Apparatus for adjusting the body temperature of a patient, said apparatus comprising:

an enclosure defining an interior space for receiving at least a portion of a patient's body therein, said enclosure having an inlet for receiving heat transfer liquid into said interior space for flow over the patient's body in direct liquid contact therewith to promote heat transfer between the patients body and said heat transfer liquid, and an outlet in fluid communication with the interior space of the enclosure for exhausting said heat transfer liquid from the enclosure, said enclosure comprising a liquid impermeable outer layer and a porous layer comprising a body-facing layer, said porous layer being capable of carrying said liquid throughout the enclosure.

74. Apparatus for adjusting the body temperature of a patient, said apparatus comprising:

an enclosure defining an interior space for receiving at least a portion of a patient's body therein, said enclosure having an inlet for receiving heat transfer liquid portion said interior space for flow over the patient's body in direct liquid contact therewith to promote heat transfer between the patient's body and said heat transfer liquid, and an outlet in fluid communication with the interior space of the enclosure for exhausting said heat transfer liquid from the enclosure, a helmet for engaging the head of the patient for circulating said liquid in contact with the head of the patient, said helmet being adapted for sealing engagement with said head of the patient, the interaction of said helmet and said head forming a void between said helmet and said head such that liquid may flow through the void and contact said head to alter the temperature of said head; and a mask for placement over the face of the patient for delivery of air to the mouth or nose of the patient.

75. A method for controlling the body temperature of a patient during a cardiopulmonary resuscitation procedure, said method comprising the steps of:

enclosing at least a portion of the patient's body within the interior space of an enclosure;

directing a heat transfer liquid to flow within the interior space in direct liquid contact with the patient's body to promote heat transfer between the heat transfer liquid and the patient's body; and performing cardiopulmonary resuscitation upon the patient simultaneous with the directing step.

* * * * *